United States Patent
Shin et al.

(10) Patent No.: US 11,261,482 B2
(45) Date of Patent: Mar. 1, 2022

(54) COMPOSITION FOR DETECTING EPIDERMAL CELL GROWTH FACTOR RECEPTOR GENE MUTATION, AND KIT COMPRISING SAME

(71) Applicant: GENCURIX INC., Seoul (KR)

(72) Inventors: Young Kee Shin, Seoul (KR); Bohyun Byun, Seoul (KR); Hyunjeung Choi, Seoul (KR); Joon Seok Choi, Seoul (KR); Young Ho Moon, Seoul (KR); Jong Heun Lee, Seoul (KR); Sang Rea Cho, Seoul (KR); Jee Eun Kim, Seoul (KR); Myungsun Kim, Seoul (KR)

(73) Assignee: GENCURIX INC, Seoul (KR)

( * ) Notice: Subject to any disclaimer, the term of this patent is extended or adjusted under 35 U.S.C. 154(b) by 299 days.

(21) Appl. No.: 16/304,340

(22) PCT Filed: May 25, 2017

(86) PCT No.: PCT/KR2017/005467
§ 371 (c)(1),
(2) Date: May 21, 2019

(87) PCT Pub. No.: WO2017/204577
PCT Pub. Date: Nov. 30, 2017

(65) Prior Publication Data
US 2019/0352703 A1 Nov. 21, 2019

(30) Foreign Application Priority Data
May 25, 2016 (KR) .................. 10-2016-0064259

(51) Int. Cl.
C12Q 1/68 (2018.01)
C07H 21/04 (2006.01)
C12Q 1/6827 (2018.01)
C12Q 1/6823 (2018.01)
C12Q 1/686 (2018.01)
C12Q 1/6874 (2018.01)
C12Q 1/6886 (2018.01)

(52) U.S. Cl.
CPC ........... *C12Q 1/6827* (2013.01); *C12Q 1/686* (2013.01); *C12Q 1/6823* (2013.01); *C12Q 1/6874* (2013.01); *C12Q 1/6886* (2013.01); *C12Q 2600/106* (2013.01); *C12Q 2600/118* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

2014/0272953 A1  9/2014  Klughammer et al.

FOREIGN PATENT DOCUMENTS

| KR | 1020140033854 A | 3/2014 |
| KR | 10-1582944 B1 | 1/2016 |
| KR | 10-2017-0009603 A | 1/2017 |

OTHER PUBLICATIONS

Roma et al., "Detection of EGFR Mutations by TaqMan Mutation Detection Assays Powered by Competitive Allele-Specific TaqMan PCR Technology", BioMed Research International, 2013, pp. 1-9, vol. 2013, Article ID 385087.
Wang H et al., "Allele-Specific, Non-Extendable Primer Blocker PCR (AS-NEPB-PCR) for DNA Mutation Detection in Cancer", The Journal of Molecular Diagnostics, Jan. 2013, pp. 62-69, vol. 15, No. 1.
International Search Report dated Sep. 29, 2017 for PCT/KR2017/005467.
Shyamala Maheswaran, Ph.D. et al., "Detection of Mutations in EGFR in Circulating Lung-Cancer Cells," The New England Journal of Medicine, Jul. 24, 2008, vol. 359, No. 4, pp. 366-377.

*Primary Examiner* — Jeanine A Goldberg
(74) *Attorney, Agent, or Firm* — Cantor Colburn LLP

(57) ABSTRACT

The present invention relates to a composition for detecting an epidermal cell growth factor receptor gene mutation and to a kit comprising the composition and, more specifically, to a primer and probe set composition for detecting an epidermal cell growth factor gene mutation, and to a kit for detecting an EGFR gene mutation, comprising the composition. A method according to the present invention can not only predict and diagnose responsiveness to a therapeutic agent for the prognosis of a cancer patient, but also predict a cancer metastasis or relapse Thus, the method can be useful for the purposes of determining the need to administer an anticancer therapeutic agent and guiding the direction of future treatment, and for monitoring a cancer metastasis or relapse.

13 Claims, 9 Drawing Sheets
Specification includes a Sequence Listing.

FIG. 1

COMPOSITION FOR DETECTING EPIDERMAL CELL GROWTH FACTOR RECEPTOR GENE MUTATION, AND KIT COMPRISING SAME

TECHNICAL FIELD

The present application claims priority from Korean Patent Application No. 10-2016-0064259, filed on May 25, 2016, the entire content of which is incorporated herein by reference.

The present invention relates to a composition for detecting epidermal cell growth factor receptor gene mutation, and kit comprising the composition. More specifically, the present invention relates to a composition of a set of primers and a probe for detecting epidermal growth factor receptor (EGFR) gene mutation and a kit for detecting an EGFR gene mutation comprising the composition.

BACKGROUND OF THE INVENTION

Cancer refers to a group of abnormal cells caused by continuous division and proliferation through a disrupted balance between cell division and death by various causes, and is also called a tumor or neoplasm. It generally develops in more than 100 parts of the body, including organs, white blood cells, bones, lymph nodes, etc., and develops into serious conditions through the phenomenon of invasion into surrounding tissues and metastasis to other organs.

Cancer therapy has been being developed continuously, and thus dozens of therapies are currently available for various cancers in clinical. However, until now, clinicians have been suffering from two difficulties. First, it takes several weeks for any therapeutic agent to take effect, and thus it is hard to know in advance about the efficacy of the therapeutic agent for each patient. That is, the therapeutic effects of any anticancer drugs can't be judged within a few days since they gradually appear over several weeks, so it takes a long time to judge the efficacy of a prescribed drug. Thereafter, if such therapeutic effect is determined to be insufficient, a different therapeutic agent will be considered. It the clinician s unable to select an appropriate therapeutic agent for a patient at the start of treatment, it will take longer for a successful treatment. This has a devastating effect on disease progression, recurrence and prognosis.

Second, there are a number of patients who do not respond to certain therapeutic agent treatment. For example, lapatinib, an anti-breast cancer agent, has been shown to have its therapeutic effects when used for patients with high levels of HER2 protein (HER2 positive) and low levels of EGFR protein. However, patients with metastatic HER2 negative breast cancer have been reported to not respond to lapatinib, indicating that lapatinib is ineffective to those patients. Based on these studies, patients with breast cancer are required to know exactly whether their cancers are HER2 negative or positive through appropriate pre-treatment assessment, so that appropriate treatment can be selected.

Therefore, if a response to a certain therapeutic agent and its side effects can be predicted in advance, it will be possible to lower treatment the dropout rate and improve the compliance of a patient due to the selection of an inappropriate drug. It will also avoid a time span for the effect of a drug to appear and the risk of adverse side effects that the patient may experience.

On the other hand, epidermal growth factor receptor (EGFR) is a type of protein tyrosine phosphorylase of the erbB receptor class. Upon the binding of a growth factor ligand, such as an epidermal growth factor (EGF), its receptor may form a homodimer with another EGFR molecule or may form a heterodimer with another class member such as erbB2 (HER2), erbB3 (HER3), or erbB4 (HER4).

The formation of homodimers and/or heterodimers of erbB receptors results in the phosphorylation of key tyrosine residues in the intracellular domain and induces the stimulation of various intracellular signaling pathways involved in cell proliferation and survival. Deregulation of erbB class signaling promotes proliferation, invasion, metastasis, angiogenesis and tumor cell survival and is described in relation to various human cancers, including lung cancer, head and neck cancer and breast cancer.

Therefore, the erbB class represents a reasonable target for the development of anti-cancer drugs, while a number of agents targeting EGFR, including gefitinib (IRESSA™) and erlotinib (TARCEVA™), are currently clinically available. In 2004, activation mutations in EGFR were reported to correlate with a responsiveness to gefitinib therapy in non-small cell lung cancer (NSCLC) (Science [2004] Vol. 304, 1497-500 및 New England Journal of Medicine [2004] Vol. 350, 2129-39). The most common EGFR activation mutations, L858R and delE746_A750, are known to be associated with responsiveness to small molecule tyrosine kinase inhibitors, such as gefitinib and erlotinib, as compared to wild-type (WT) EGFR. Ultimately, acquired tolerance to therapy using gefitinib or erlotinib may occur. For example, when a mutation of the gatekeeper residue T790M occurs, it is known to develop a drug resistance to gefitinib and erlotinib, while such mutation has been reported to be detected clinically in 50% of patients with such drug resistance.

Thus, the presence of the EGFR mutation acts as a strong predictor of drug sensitivity in response to EGFR kinase inhibitors such as gefitinib and erlotinib, and therefore an effective and rapid detection method of the EGFR mutation is required for an optimal therapeutic approach.

Therefore, the present inventors developed a set of primers/probe and a kit containing the same that detects EGFR gene mutation suitable for its application to cfDNA in blood (Liquid biopsy) of a patient (known Patent Application No. 10-2015-0101915). However, due to a demand for detecting the EGFR gene mutation more efficiently and accurately, it is required to study additional set of primers/probe and mutation sites where EGFR inhibitors other than gefitinib and erlotinib act.

Multiple papers and patent documents are referred to throughout this specification and their citations are indicated. The disclosures of the cited papers and patent documents are incorporated herein by reference in their entirety to better understand the state of the art to which the present invention pertains and the content of the present invention.

DETAILED DESCRIPTION OF THE INVENTION

Technical Problem

Accordingly, the present inventors have developed rapidly detecting EGFR mutation to select a drug treatment strategy for EGFR-related cancer patients, a set of primers/probe and a kit containing the same suitable for detecting the EGFR gene mutation which can be used for metastasis or recurrence of cancer or for monitoring in order to present, thereby completing the present invention.

Accordingly, an aspect of the present invention is to provide a composition of a set of primers and a probe for detecting an EGFR (epidermal growth factor receptor) gene mutation.

Another aspect of the present invention is to provide a kit for detecting an EGFR (epidermal growth factor receptor) gene mutation, the kit comprising a composition of a set of primers and a probe for detecting an EGFR (epidermal growth factor receptor) gene mutation.

Another aspect of the present invention is to provide use of the composition for the preparation of an agent for detecting an epidermal growth factor receptor (EGFR) mutation.

Another aspect of the present invention is to provide a method for detecting an EGFR gene mutation, the method comprising the steps of:

(a) isolating DNA from a sample;
(b) performing PCR on the isolated DNA as a template with the composition of a set of the primers and probe of any one of claims 1 to 5; and
(c) detecting an epidermal growth factor receptor (EGFR) gene through a product amplified by the PCR.

Another aspect of the present invention is to provide a method for evaluating a therapeutic responsiveness to an EGFR inhibitor in an EGFR inhibitor-administered patient, the method comprising the steps of:

(a) isolating DNA from a sample;
(b) performing PCR on the isolated DNA as a template with the composition of a set of the primers and probe of any one of claims 1 to 5;
(c) measuring the mutation index (mutation frequency) of a product amplified by the PCR; and
(d) comparing the measured mutation index (mutation frequency) with a previously measured mutation index, thereby determining whether the measured mutation index is decreased or increased, wherein an increase in the mutation index is evaluated as an increase in cancer cells or in resistance to a therapeutic agent, whereas a decrease in the mutation index is evaluated as a decrease in cancer cells or a maintenance of susceptibility to a therapeutic agent.

Technical Solution

An embodiment according to an aspect of the present invention provides a composition of a set of primers and a probe for detecting an EGFR (epidermal growth factor receptor) gene mutation.

An embodiment according to another aspect of the present invention provides a kit for detecting an EGFR (epidermal growth factor receptor) gene mutation, the kit comprising a composition of a set of primers and a probe for detecting an EGFR (epidermal growth factor receptor) gene mutation.

An embodiment according to another aspect of the present invention provides use of the composition for the preparation of an agent for detecting an epidermal growth factor receptor (EGFR) mutation.

An embodiment according to another aspect of the present invention provides a method for detecting an EGFR gene mutation, the method comprising the steps of:

(a) isolating DNA from a sample;
(b) performing PCR on the isolated DNA as a template with the composition of a set of the primers and probe of any one of claims 1 to 5; and
(c) detecting an epidermal growth factor receptor (EGFR) gene through a product amplified by the PCR.

An embodiment according to another aspect of the present invention provides a method for evaluating a therapeutic responsiveness to an EGFR inhibitor in an EGFR inhibitor-administered patient, the method comprising the steps of:

(a) isolating DNA from a sample;
(b) performing PCR on the isolated DNA as a template with the composition of a set of the primers and probe of any one of claims 1 to 5;
(c) measuring the mutation index (mutation frequency) of a product amplified by the PCR; and
(d) comparing the measured mutation index (mutation frequency) with a previously measured mutation index, thereby determining whether the measured mutation index is decreased or increased, wherein an increase in the mutation index is evaluated as an increase in cancer cells or in resistance to a therapeutic agent, whereas a decrease in the mutation index is evaluated as a decrease in cancer cells or a maintenance of susceptibility to a therapeutic agent.

Unless otherwise defined, all technical and scientific terms used herein have the same meaning as commonly understood by one of ordinary skill in the art to which this presently described subject matter belongs. The following references provide one of the skills with a general definition of the various terms used in the specification of the present invention: Singleton et al., DICTIONARY OF MICROBIOLOGY AND MOLECULAR BIOLOGY (2th ed. 1994); THE CAMBRIDGE DICTIONARY OF SCIENCE AND TECHNOLOGY(Walker ed., 1988); 및 Hale & Marham, THE HARPER COLLINS DICTIONARY OF BIOLOGY.

Hereinafter, the present invention will be described in detail.

The present invention provides a composition of a set of primers and a probe for detecting an EGFR (epidermal growth factor receptor) gene mutation, the composition comprising at least one polynucleotide set selected from the group consisting of the following sets as an active ingredient:

i) a polynucleotide set of a forward primer of SEQ ID NO: 3, a reverse primer of SEQ ID NO: 4, a forward primer of SEQ ID NO: 5, a reverse primer of SEQ ID NO: 6, and a probe defined by one selected from the group consisting of SEQ ID NOS: 16 to 20;

ii) a polynucleotide set of a forward primer of SEQ ID NO: 7, a reverse primer of SEQ ID NO: 8, a forward primer of SEQ ID NO: 11, a reverse primer of SEQ ID NO: 12 and a probe defined by one selected from the group consisting of SEQ ID NOs: 21, 28 and 30;

iii) a polynucleotide set of a forward primer of SEQ ID NO: 1, a reverse primer of SEQ ID NO: 2, a forward primer of SEQ ID NO: 7, a reverse primer of SEQ ID NO: 8 and a probe defined by one selected from the group consisting of SEQ ID NOs: 13 to 15, 22, 23 and 35; and iv) a polynucleotide set of a forward primer of SEQ ID NO: 9, a reverse primer of SEQ ID NO: 10, a forward primer of SEQ ID NO: 11, a reverse primer of SEQ ID NO: 12, and a probe defined by one selected from the group consisting of SEQ ID NOS: 24 to 27, 29.

The compositions of the present invention are preferably characterized by predicting a therapeutic responsiveness to EGFR inhibitors. Since the mutation in EGFR was reported to correlate with the therapeutic responsiveness to zetifinib therapy in non-small-cell lung cancer (NSCLC) in 2004 (Science [2004] Vol. 304, 1497-500 및 New England Journal of Medicine [2004] Vol. 350, 2129-39), a number of related EGFR mutations have been identified.

As used herein, 'epidermal growth factor receptor (EGFR)' is a protein product of erbB or ErbB1 which is oncogene, while erbB or ErbB1 is one of ERBB group which is a protooncogenes. It has been observed that the expression of EGFR is increased in lung cancer, breast cancer, bladder cancer, stomach cancer and the like.

As used herein, 'EGFR inhibitor' is an EGFR target drug for treating epithelial cell cancer such as lung cancer, breast cancer, bladder cancer, stomach cancer and the like, while in particular Gefitinib (AstraZeneca UK Ltd., trade name "IRESSA"), Erlotinib (Genentech, Inc. & OSI Pharmaceuticals, Inc., trade name "TARCEVA"), Afatinib (Boehringer Ingelheim GmbH corp., trade name "GIOTRIF"), and Osimetinib (AstraZeneca UK Ltd., trade name "TAGRISSO") are representative drugs. In addition, EAI045 (CAS No. 1942114-09-1), an EGFR Tyrosine kinase inhibitor with a drug responsiveness to drug-resistant T790M/C797S mutation and C797S mutation, is under development (Cancer letter [2017] Vol. 385, 51-54 및 nature letter [2016] Vol. 534, 129-132). Gefitinib and Erlotinib are quinazoline compounds that inhibit tyrosine kinase activity of EGFR and prevents cell growth by inhibiting phosphorylation. More preferably, the EGFR inhibitor may be erlotinib, gefitinib, Afatinib, osimertinib or EAI045 (CAS No. 1942114-09-1), but is not limited thereto.

As used herein, 'therapeutic responsiveness' may be defined as 'responsiveness' to a therapeutic agent if the growth rate of the cancer is inhibited as a result of contact with the therapeutic agent as compared to the growth of cancer in the case of no contact with the therapeutic agent. It may be defined as 'non-responsiveness' to the therapeutic agent, if the growth rate of the cancer is inhibited to a very low extent or not inhibited at all as a result of contact with the therapeutic agent as compared to growth in the case of no contact with the therapeutic agent. The growth of cancer may be measured in a various ways, including by measuring the size of a tumor or the expression of an appropriate tumor marker. In addition, the 'responsiveness' may indicate a significant increase in survival time on a survival curve, while the 'non-responsiveness' scale may be assessed using additional criteria beyond the size of the tumor, including the patient's quality of life, metastasis, and so on.

More preferably, the therapeutic responsiveness is a therapeutic responsiveness to an inhibitor of epidermal growth factor receptor (EGFR), and thus the cancer of the present invention may be lung cancer, breast cancer, bladder cancer or stomach cancer.

As used herein, the term 'primer' means an oligonucleotide which can act as a starting point for synthesis under a condition of inducing the synthesis of a primer extension product complementary to a nucleic acid chain (template), that is, the presence of a polymerization such as a nucleotide and a DNA polymerase, and suitable temperature and pH conditions. Preferably, the primer is a deoxyribonucleotide and is a single strand. The primers used in the present invention may include naturally occurring dNMPs (i.e., dAMP, dGMP, dCMP, and dTMP), modified nucleotides or non-natural nucleotides. In addition, the primer may also include ribonucleotides.

The primer should be long enough to be able to prime the synthesis of the extension product in the presence of the polymerization. The suitable length of the primer is determined by a number of factors, such as a temperature, an application, and a source of the primer, while being typically 15-30 nucleotides. Short primer molecules generally require lower temperatures to form a sufficiently stable hybrid complex with the template. The term 'annealing' or 'priming' means that oligodeoxynucleotides or nucleic acids are apposite to the template nucleic acid, while such the 'apposition' allows the polymerase to polymerize the nucleotides to form complementary nucleic acid molecules in the template nucleic acid or a portion thereof.

As used herein, the term 'probe' is designed as a kind of taqman probe used for quantitative PCR. Preferably, a fluorescent material (HEX, VIC, FAM dye) is attached to the probe, while BHQ1 may be used as a quencher on the 3' side of any probes. The TaqMan probe is an oligonucleotide tagged with a fluorescent substance at the 5' end and a quencher substance at the 3' end, respectively. The TaqMan probe specifically hybridizes to template DNA in an annealing step, but does not exhibit fluorescence even when light is applied, because there is a quencher at the 3' end of the probe. In the following extension step, the 5'→3' exonuclease activity of Taq DNA polymerase degrades the TaqMan probe hybridized to the template. Then, the fluorescent substance is separated from the probe, the inhibition by the quencher is released, fluorescence is showed. Through such a principle the fluorescence due to PCR reaction is quantitatively shown.

The probe of the present invention is bound to a fluorescent material, more preferably HEX (hexachlorofluorescein), FAM (fluorescein amidite) or EverGreen fluorescent dye.

Specifically, since the probe is combined with FAM, HEX fluorescent dye (fluorescent substance) or EvaGreen fluorescent dye, measuring the compined fluorescence may be performed. Such a process can be performed by a commercial detector (for example, Droplet Reader from biorad), and the droplet fluorescence signal of each sample can be detected in the apparatus, and the number of positive and negative droplets can be counted, and the analysis can be completed automatically.

In this case, probes to be added to PCR reaction solution and the standard PCR reaction solution may be respectively bound with different fluorescent materials.

The present invention provides a kit for detecting an EGFR gene mutation, the kit comprising a set of primers and a probe according to the present invention.

The kit of the present invention further comprises an oligomer (blocker) designed to prevent the non-specific binding of the probe for mutation detection to a wild-type sequence using the wild-type sequence corresponding to the mutation position, in order to reduce background noise.

The kit of the present invention can be preferably used for the detection of the EGFR gene mutations by PCR reaction using the primers/probe set of the present invention. The kit of the present invention may further comprise apparatus and/or reagents known in the art used for PCR or detection thereof. The kit of the present invention may further comprise a tube, a well plate, an instructional material describing a method of use, etc., to be used for mixing the components as required.

In addition, the kit of the present invention may be a research use only (RUO) kit or an in vitro diagnostics (IVD) kit. The IVD kits also include in vitro companion diagnostics (IVD-CDx) kits.

The present invention provides a kit for detecting an EGFR gene mutation, the kit comprising a polynucleotide set of a forward primer of SEQ ID NO: 3, a reverse primer of SEQ ID NO: 4, a forward primer of SEQ ID NO: 5, a reverse primer of SEQ ID NO: 6, and a probe defined by one selected from the group consisting of SEQ ID NOS: 16 to 20 as an active ingredient.

Also, the present invention provides a kit for detecting an EGFR gene mutation, the kit comprising a polynucleotide set of a forward primer of SEQ ID NO: 7, a reverse primer of SEQ ID NO: 8, a forward primer of SEQ ID NO: 11, a reverse primer of SEQ ID NO: 12, and a probe defined by one selected from the group consisting of SEQ ID NOS: 21, 28 and 30 as an active ingredient.

Also, the present invention provides a kit for detecting an EGFR gene mutation, the kit comprising a polynucleotide set of a forward primer of SEQ ID NO: 1, a reverse primer of SEQ ID NO: 2, a forward primer of SEQ ID NO: 7, a reverse primer of SEQ ID NO: 8, and probe defined by one selected from the group consisting of SEQ ID NOS: 13 to 15, 22, 23 and 35 as an active ingredient.

Also, the present invention provides a kit for detecting an EGFR gene mutation, the kit comprising a polynucleotide set of a forward primer of SEQ ID NO: 9, a reverse primer of SEQ ID NO: 10, a forward primer of SEQ ID NO: 11, a reverse primer of SEQ ID NO: 12, and probe defined by one selected from the group consisting of SEQ ID NOS: 24 to 27, 29 as an active ingredient.

The kit of the present invention is used for quantitative PCR (qPCR) or digital PCR method.

Any templates applicable to the kits of the present invention may be used without limitation as long as detection of EGFR mutation is required for and PCR reaction is possible. Preferably, the template is cell-free DNA (cfDNA) isolated from blood (Liquid biopsy), DNA isolated from formalin-fixed paraffin embedded (FFPE) tissue, or complementary DNA (cDNA) synthesized by reverse transcription from RNA derived from the tissue.

cfDNA circulating in human plasma has been studied in a variety of physiological and pathological conditions such as inflammatory disorders, oxidative stress and malignant tumors. The precise mechanism involved in the bloodstream release of cfDNA is uncertain, but appears to be an overall effect of apoptosis, cell necrosis and active release from cells. cfDNA circulating through blood vessels is a potentially useful biomarker. DNA levels and fragmentation patterns present interesting potential for diagnostic and prognostic prediction purposes. In particular, since such biomarker can be easily detected from the patient's blood, it is useful to detect such biomarker easily and rapidly without deteriorating the quality of life.

The tissue obtained from a patient after biopsy is usually fixed with formalin (formaldehyde) or the like. The immobilized biological sample is generally dehydrated and embedded in a solid support such as paraffin, and the prepared sample is called a formalin-fixed paraffin-embedded (FFPE) sample. Nucleic acids, especially DNA, on FFPE samples are present in immobilized cells and are either fragmented or cross-linked by formalin. Therefore, it is necessary to remove paraffin and dissolve immobilized cells to elute nucleic acids including DNA from the cells.

As used herein, the term 'paraffin' refers to encompass the embedded medium of a biological sample used in all types of analyses including morphological, immunohistochemical and enzymatic histochemical analysis. That is, the paraffin in the present invention may be a petroleum-based paraffin wax unit substance, or may contain other components that can be added for the purpose of improving the quality of the embedded medium, using the petroleum-based paraffin wax as a base materials. Herein, the petroleum-based paraffin wax refers to a mixture of hydrocarbons derived from petroleum which are solid at room temperature.

Generally, a FFPE-treated sample of a cancer patient is cut to a thickness of 5 to 10 μm using a rotary microtome, and then the nucleic acid containing DNA can be isolated through a commercially available nucleic acid separation kit for FFPE or an apparatus utilizing the same. Kits/devices for separating nucleic acids from FFPE include, for example, the Tissue Preparation System from Siemens and related reagents (VERSANT tissue preparation reagents).

The kit of the present invention may use, as a template, DNA isolated from circulating tumor cell (CTC) separated from blood (Liquid biopsy) or complementary DNA (cDNA) synthesized by reverse transcription from RNA derived from CTC.

A 'circulating tumor cell (CTC)', which can be used as a template in the present invention, is a tumor cell found in the peripheral blood of a malignant tumor patient, and plays an important role in the process of metastasis. CTC is considered to be very important for the study and diagnosis of cancer, but the amount of CTC is very low in the peripheral blood, and there is a need for a detection system that requires such a high degree of sensitivity to detect dozens or fewer tumor cells mixed with more than a million normal blood cells.

The nucleic acid isolated from the sample according to the present invention is preferably a genomic DNA, more preferably a genomic DNA which is suspected to have a mutation.

The compositions or kits of the present invention can preferably be used for EGFR mutation detection in automated or semi-automated methods. As used herein, the automated method means that all or most of the processes except input of a sample; relocation or movement of a substrate (for example, tube, plate) that has been extracted, separated, or reacted; reagent, placement into a stock of buffers, and their supplementation; maintenance of equipment are performed through non-manual means (for example, robot).

In an embodiment of the present invention, it was confirmed that the composition or kit of the present invention showed an excellent mutation-detecting ability for the cfDNA sample and FFPE sample in the detection of the EGFR gene mutation (see Example 10).

The following references can be referred to for the above-mentioned nucleotide work (Maniatis et al., Molecular Cloning: A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press(1989); Deutscher, M., Guide to Protein Purification Methods Enzymology, vol. 182. Academic Press. Inc., San Diego, Calif. (1990); Ausubel et al., Current Protocols of Molecular Biology, John Wiley and Sons(1997); Rupp and Locker, Lab Invest. 56: A67(1987); De Andres et al., BioTechniques 18: 42044(1995); Held et al., Genome Research 6:986-994(1996); T. E. Godfrey et al. J. Molec. Diagnostics 2: 84-91(2000); K. Specht et al., Am. J. Pathol. 158: 419-29(2001)).

The present invention provides use of the composition of a set of primers and a probe for the preparation of an agent for detecting an epidermal growth factor receptor (EGFR) gene mutation.

The present invention provides a method for detecting an EGFR gene mutation, the method comprising the steps of:

(a) isolating DNA from a sample;

(b) performing PCR on the isolated DNA as a template with the composition of a set of the primers and probe of any one of claims 1 to 5; and (c) detecting an epidermal growth factor receptor (EGFR) gene through a product amplified by the PCR.

As used herein, the term 'sample' includes blood and other liquid samples having biological origins, biopsy samples, solid tissue samples such as tissue culture, or cells derived therefrom. More specifically, examples of the sample may include, but are not limited to, tissues, extracts, cell lysates, whole blood, plasma, serum, saliva, ocular fluid, cerebrospinal fluid, sweat, urine, milk, ascites fluid, synovial fluid, peritoneal fluid, and the like. The sample may be obtained from animals, preferably mammals, and most preferably humans. The sample may also be pre-treated before its use for detection. For example, the sample may be pre-treated by filtration, distillation, extraction, concentration, the inactivation of interfering components, the addition of reagents, and the like. Preferably CTC, blood (Liquid biopsy), formalin fixed paraffin embedded (FFPE) or fresh sample, etc. obtained from the patient, most preferably blood (Liquid biopsy) or formalin fixed paraffin embedded (FFPE) sample obtained from the patient. As described above, a genomic DNA or DNA suspected of having a mutation can be isolated from the sample and used for EGFR gene mutation detection.

As described above, the detection method of the present invention is for predicting a therapeutic responsiveness of EGFR inhibitors such as erlotinib, gefitinib, afatinib, osimertinib, and target tyrosine kinase inhibitor for C797S, EGFR gene mutations may be detected by qPCR (quantitative PCR) or digital PCR method.

The present invention provides a method for evaluating a therapeutic responsiveness to an EGFR inhibitor in an EGFR inhibitor-administered patient, the method comprising the steps of:

(a) isolating DNA from a sample;

(b) performing PCR on the isolated DNA as a template with the composition of a set of the primers and probe of any one of claims 1 to 5;

(c) measuring the mutation index (mutation frequency) of a product amplified by the PCR; and (d) comparing the measured mutation index (mutation frequency) with a previously measured mutation index, thereby determining whether the measured mutation index is decreased or increased, wherein an increase in the mutation index is evaluated as an increase in cancer cells or in resistance to a therapeutic agent, whereas a decrease in the mutation index is evaluated as a decrease in cancer cells or a maintenance of susceptibility to a therapeutic agent.

As used herein, the term 'resistance to a therapeutic agent' refers to a characteristic in which a therapeutic effect is not exhibited from a treatment using the EGFR inhibitor as a target cancer treatment agent. For example, it refers to the case where the size of the tumor does not change after chemotherapy or a larger amount of drug is administered to achieve the same effect as the previous treatment. Preferably, it refers to the case where the size of the tumor does not change.

As used herein, the term 'susceptibility to a therapeutic agent' refers to a characteristic in which there is a benefit or a therapeutic effect from the treatment using the EGFR inhibitor as a target cancer treatment agent. For example, it means that the tumor size is decreased by 5%, 10%, 15%, 20%, 25%, 30% or more after the chemotherapy, and preferably the tumor size is decreased by 30% or more (which means Complete response or partial response according to RECIST (Response Evaluation Criteria in Solid Tumors), a criterion for evaluating the response of solid cancers to anti-cancer agents).

As used herein, the term 'method for evaluating a therapeutic responsiveness' is to compare the EGFR mutation rates between a measured result from the patient's blood (Liquid biopsy) or FFPE sample prior to the administration of the EGFR inhibitor and a measured result from the blood (Liquid biopsy) or FFPE sample of the same patient at a certain period of time after administering the EGFR inhibitor, thereby confirming whether the EGFR mutation rate is decreased or increased. In addition, such method may be a method of monitoring the increase or decrease of cancer cells during the period of treating the patient, and may be a method of monitoring the responsiveness to the EGFR inhibitor.

Regarding the 'certain period at time', after measuring the mutation rate using the sample initially obtained from the patient, and then measuring the mutation rate may be measured using a sample obtained from the same patient at intervals of 1 day to 1 year. Preferably, the mutation rate may be measured using a sample obtained from the same patient at intervals of 1 day to 10 months, more preferably, at intervals of 7 days to 5 months, and most preferably, at intervals of 7 days to 2 months.

As used herein, the 'EGFR mutation' may be L858R, L861Q, T790M, 19 deletion, G719X, C797S, 20 insertion and S768I, more preferably, it may be L858R, 19 deletion, or T790M.

As used herein, the 'sample' is the same as described above. Preferably, the sample may be a blood (Liquid biopsy), a circulating tumor cell (CTC), a formalin fixed paraffin embedded (FFPE), a cfDNA (cell-free DNA) and a fresh sample, most preferably, a blood (Liquid biopsy) or a FFPE.

Advantageous Effect

Accordingly, the present invention provides a composition of a set of primers and a probe for detecting epithelial growth factor receptor (EGFR) gene mutation and a kit comprising the same. The method of the present invention makes it possible to predict or diagnose the responsiveness of a cancer patient to a therapeutic agent as well as the prediction of cancer metastasis or recurrence. Therefore, the present invention can be usefully used for judging the necessity of administration of an anti-cancer agent, providing clues about the direction of future treatment and monitoring the metastasis or recurrence of cancer.

BRIEF DESCRIPTION OF DRAWINGS/FIGURES

Figure 1:
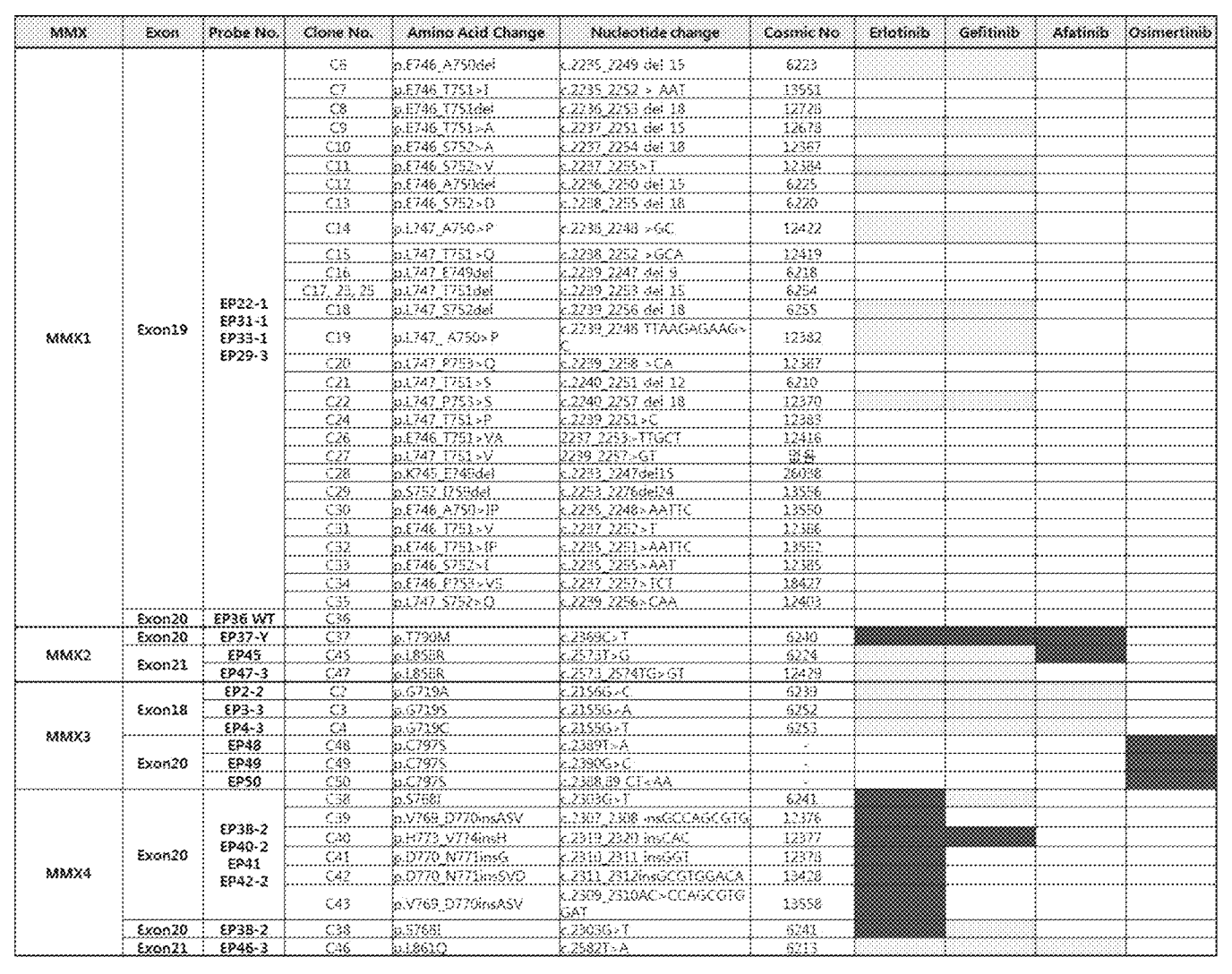

FIG. 1 shows the construction (MMX 1 to 4) of an EGFR mutation detection kit comprising a probe and primers of the present invention, and shows the types of probe and detectable EGFR mutations contained in each MMX.

MODE FOR CARRYING OUT INVENTION

Figure 2A:
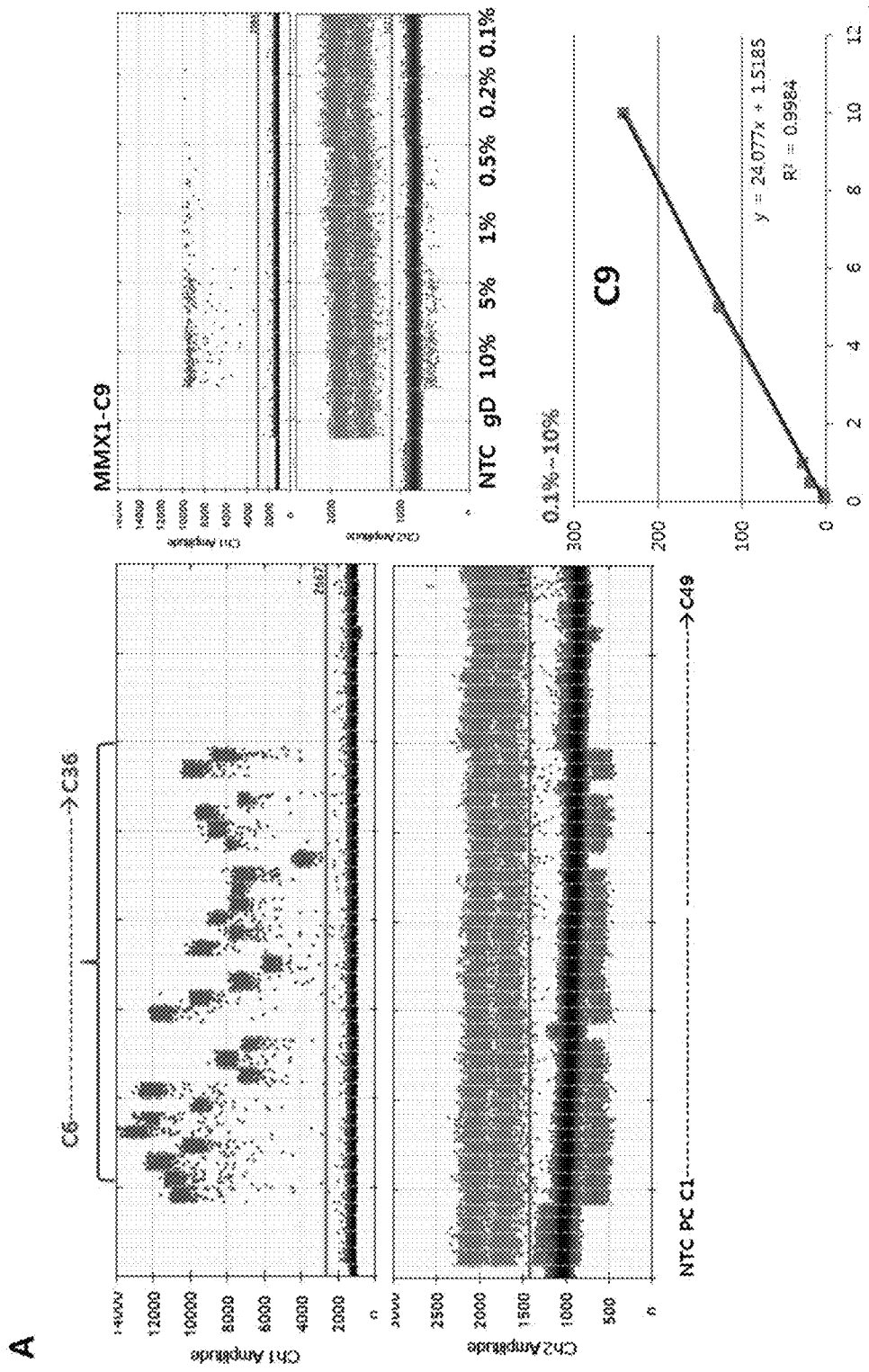
FIGS. 2A and 2B are the results of confirming whether the EGFR mutation detection kit containing the probe and the primers according to the present invention can detect forty six (46) EGFR mutation sites, while the results are only those detected in the EGFR mutation sites contained in MMX1 (FIG. 2A) and MMX2 (FIG. 2B).
Figure 2B:
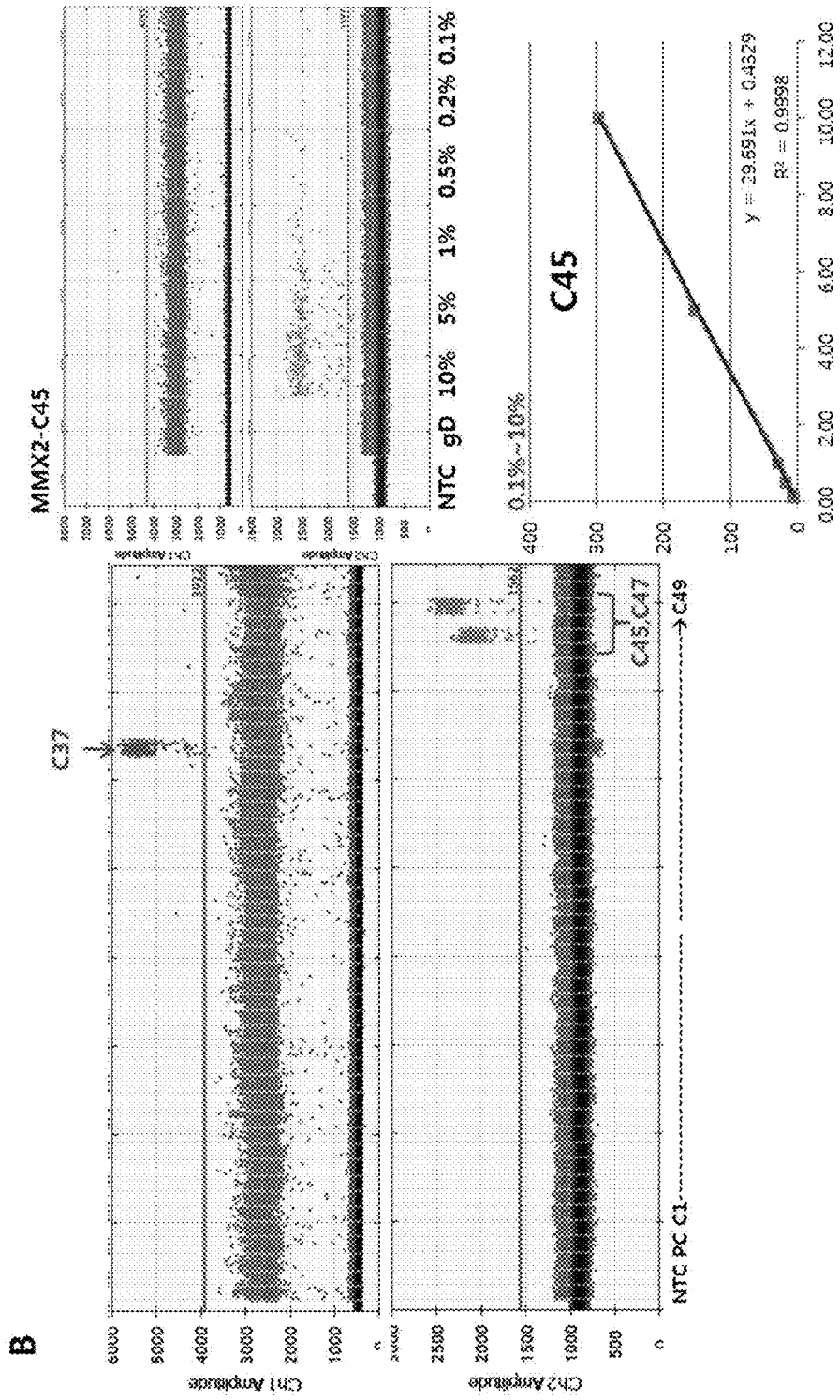
Figure 3A:
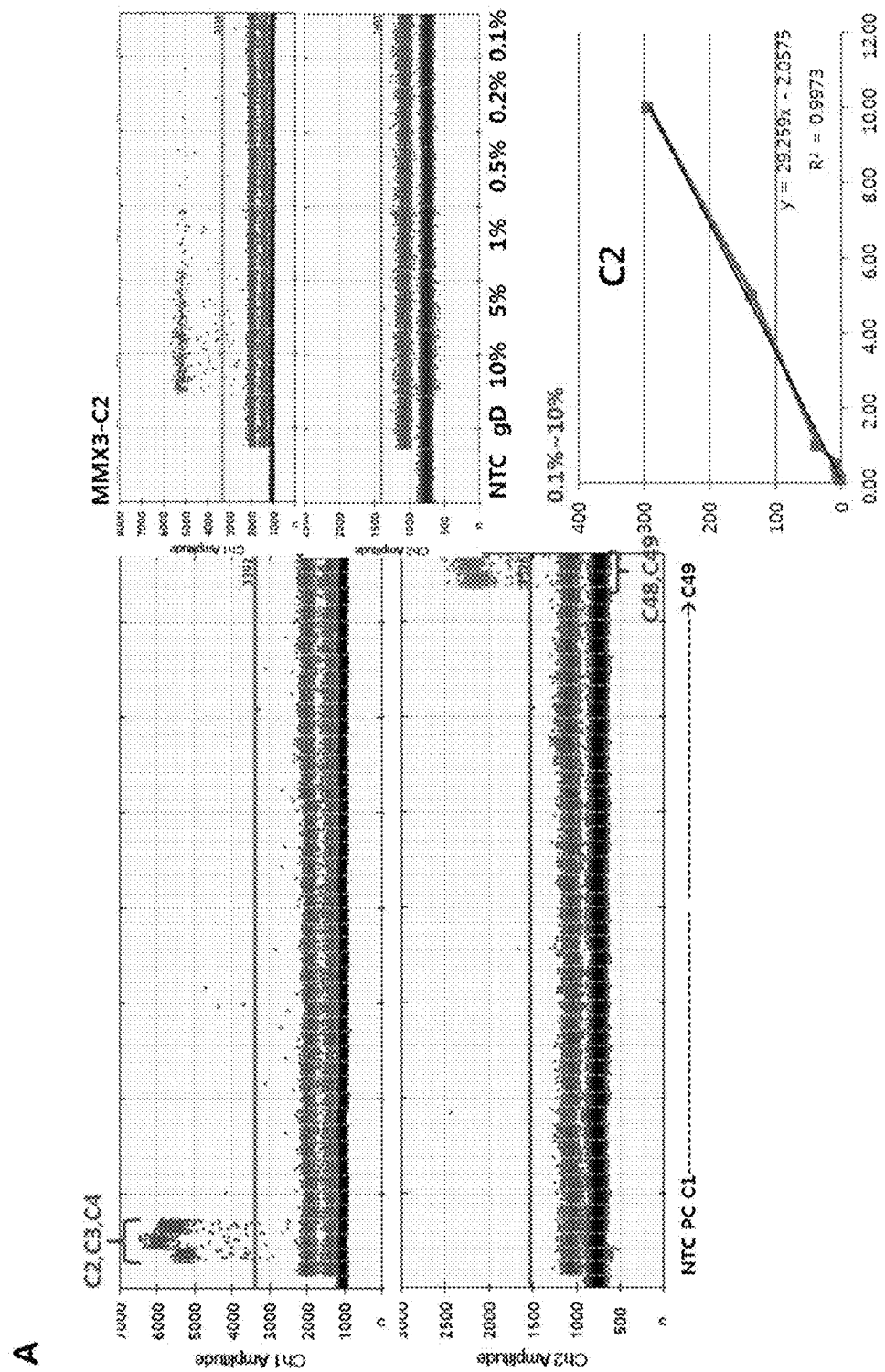
FIGS. 3A, 3B and 3C are the results of confirming whether the EGFR mutation detection kit containing the probe and the primers according to the present invention can detect forty six (46) EGFR mutation sites, while the results are only those detected in the EGFR mutation sites contained in MMX3 (FIGS. 3A and 3C) and MMX4 (FIG. 3B).
Figure 3B:
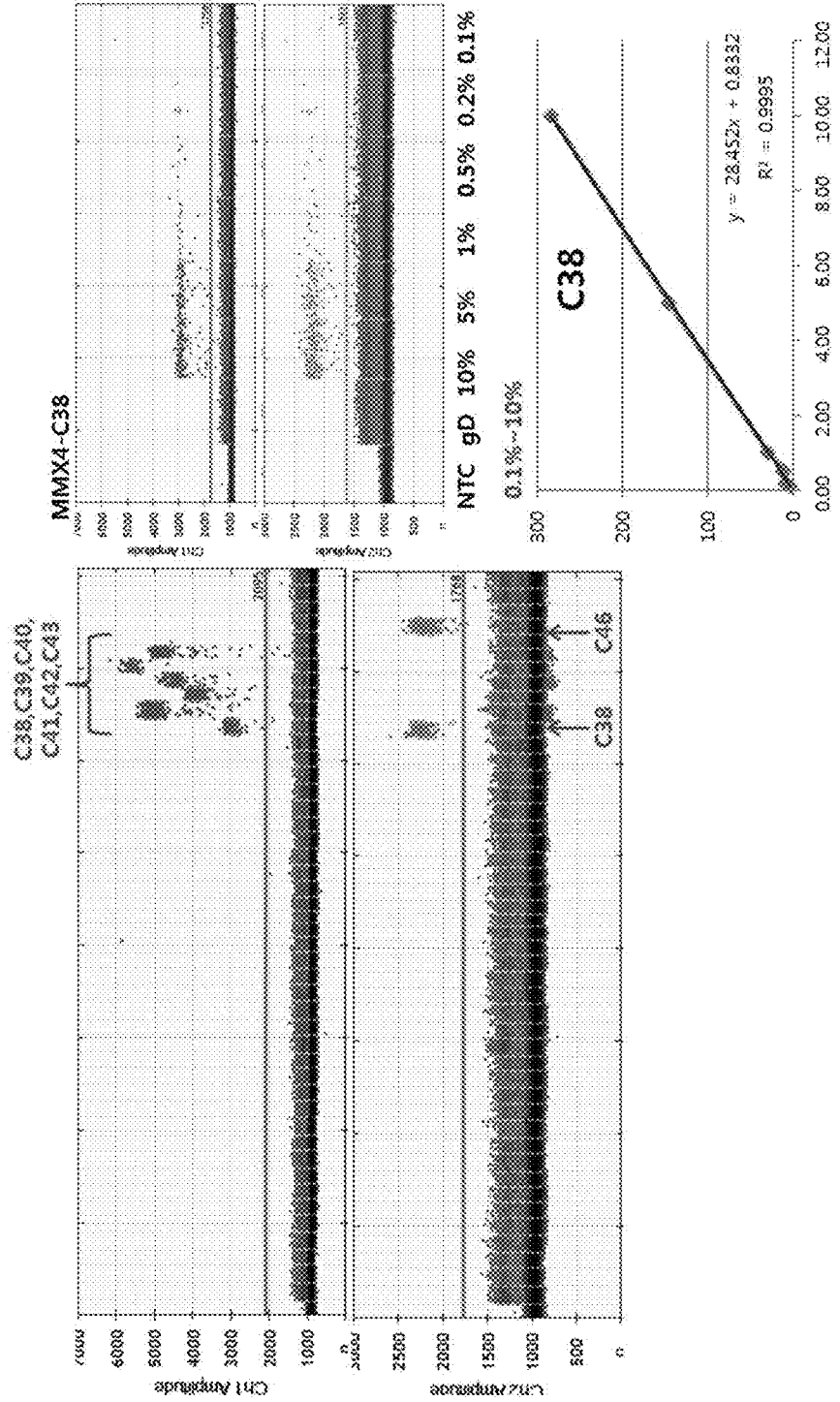
Figure 3C:
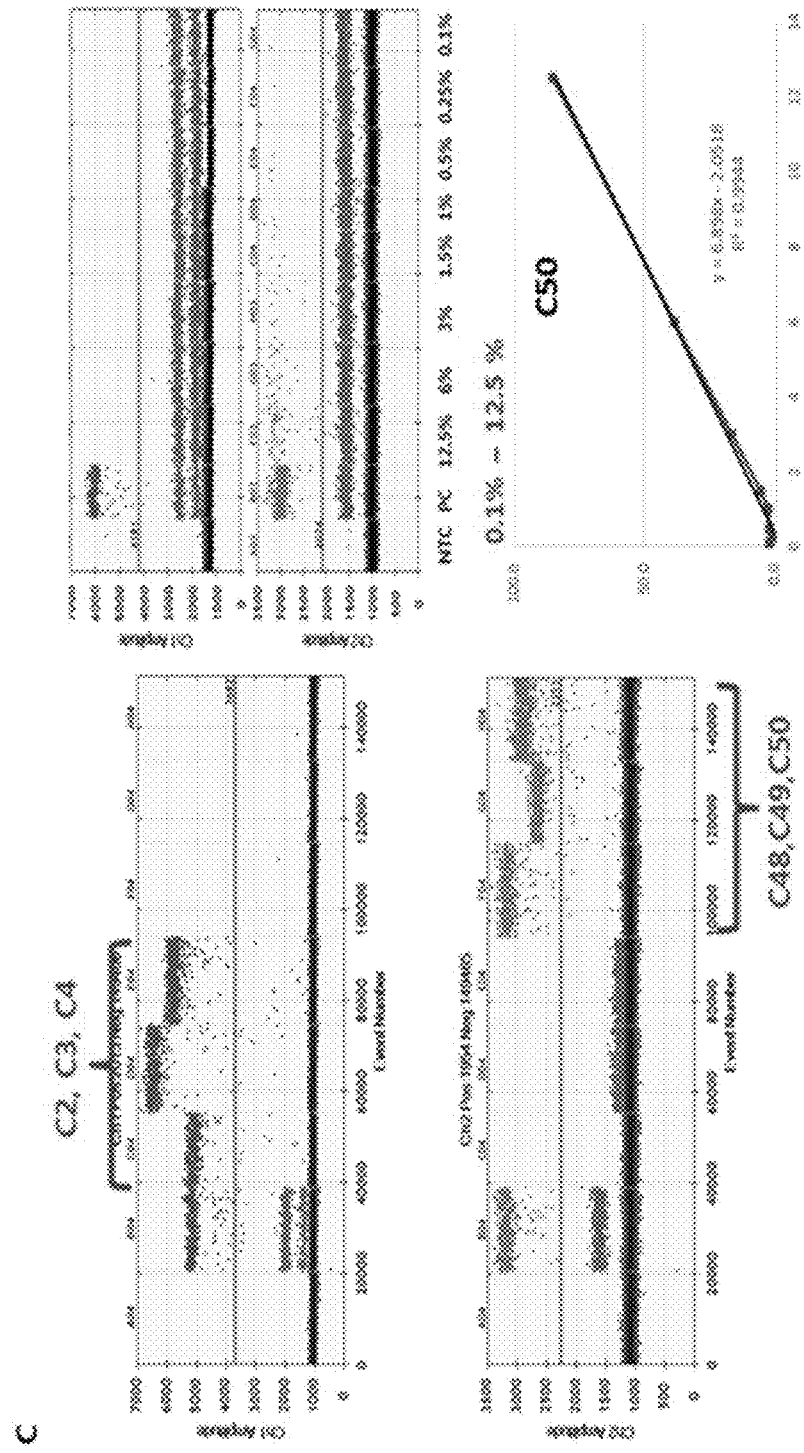

Hereinafter, the present invention will be described in detail.

However, the following examples are only illustrative of the present invention, and the present invention is not limited to the following examples.

Example 1: Isolation of Cell-Free DNA (cfDNA) from Plasma

Plasma cfDNA was isolated using a nucleic acid extraction kit (QIAGEN). The blood (Liquid biopsy) of the patient was centrifuged at 3,000 rpm for 10 minutes, and 1 ml of plasma was transferred to a 15 ml tube while taking care of the cellular debris. To this sample, 800 μl of lysis buffer and 100 μl of reconstituted protease K were mixed. After brief vortexing, the tube was incubated at 60° C. for 30 minutes. 1.8 ml of binding buffer was mixed with the sample, vortexed briefly, and reacted on ice for 5 minutes. After attaching a vacuum connection tube provided in the circulating nucleic acid kit to a vacuum pump, a column and a passing fraction tube were connected to the upper part of the vacuum connection tube. The sample was placed in the passing fraction tube and the vacuum pump was operated to pass the sample in the column. To wash the column, 700 μl of a washing solution was put in the passing fraction tube, and the vacuum pump was operated again to wash the column. The passing fraction tube and the vacuum connection tube were discarded and the column was connected to a new collection tube. Centrifugation at 14,000 rpm for 3 minutes was conducted to completely remove the washing solution in the column. After centrifugation, the column was connected to a new collection tube and the column was dried at 56° C. for 10 minutes. The column was transferred to a new 1.5 ml Eppendorf tube, and 50 μl of elution buffer was added to the center of the column, followed by incubation at room temperature for 1 minute. Thereafter, the DNA sample was eluted by centrifugation at 14,000 rpm for 1 minute at room temperature. It was stored at 4° C. until its use, or frozen at −70° C. for its long-term storage.

Example 2: Construction of Standard Material Vector

Standard material vectors (named as mini-clones) were constructed to validate designed primers and probes, and to prepare a reference material required for ddPCR. In the mini-clone preparation process, about 300 bp was synthesized by centering mutation sites or positions in each exon of EGFR, that is, probe sites or position. The synthesized DNA fragment was inserted between the universal link sequence of pIDTSmart Amp vector and the produced clone was transformed into *E. coli* DH5α cells.

In order to maximize the efficiency of the droplet digital PCR (ddPCR), the standard material vector was treated with restriction enzymes to linearize the standard material vector existing in a circular form or super-coiled form. For linearization of the standard material vector (Miniclone DNA), Cla1 or Pst1 restriction enzyme was reacted at 37° C. for 30 minutes. The reaction products were them cleaned up and stored at −20° C. until their use.

In the present invention, the level after PCR amplification of a detection target may be entirely different depending on the target sample, so a criterion for determining an amplification by primers/probe specific for a mutation is necessary. For this purpose, the standard material vector may be used, in which a polynucleotide of 100 bp to 350 bp containing genomic DNA gene mutation is transformed into a conventional vector. Preferably, the standard material vector of the present invention may be used by inserting about 300 bp in the pIDTSmart Amp vector in a region where mutations occur in each exon of EGFR, i.e., the probe position as a center.

Example 3: Resign of Selection of Primers/Probe

In order to develop a biomarker for EGFR, a lung cancer-related gene, the mutation position was confirmed based on the cosmic number (http://cancer.sanger.ac.uk). Using the primer3 program, primers for each exon of the gene was designed so that a forward primer can overlap with an intron part. The design conditions are as follows: the Tm value of the primer was 55 to 60° C. and the GC % was 40 to 62%.

The probes were designed as a taqman probe by selecting those that satisfy a condition. HEX/FAM reporter fluorescence was attached to the 5' wild type probe and HEX/FAM dye was attached to the 5' mutant probe to detect the amplification. BHQ1 was used as a quencher on the 3' side of all probes. 3, 4, 8, and 2 probes were designed and synthesized for EGFR exons 18, 19, 20, and 21, respectively. The probes designed by the present inventors have allele specificity, while most probes have cosmic numbers.

On the other hand, in order to reduce the background (noise), blocker oligomers were constructed to prevent the non-specific binding of mutation detection probes to wild-type sequences, using the wild type sequence corresponding to the mutation position.

The information of the designed primers and probes is shown in Table 1 and Table 2, respectively.

TABLE 1

Information of primers

| Primer name | Sequence | Seq. no. | Exon |
|---|---|---|---|
| C1-F1 | tgaggatcttgaagaagaaactga | 1 | Exon 18 |
| C1-R1 | ctgtgccaaagggaccttacct | 2 | Exon 18 |
| C5-F15 | ccctccaggaagcctaaacg | 3 | Exon 19 |
| C29-R1 | aggttcagagccatggacaa | 4 | Exon 19 |
| C36-F1 | ccctccaggaagcctacg | 5 | Exon 20 |
| C36-R1 | cagccgaagggcatga | 6 | Exon 20 |
| C36-F18 | ccctccaggaagcaactacg | 7 | Exon 20 |
| F36-R16 | tttgtgaattcccggacatagtc | 8 | Exon 20 |
| C36-F17 | ccacactgacgtgaacctct | 9 | Exon 20 |
| C36-R14 | ggtggaggaatgaggcagat | 10 | Exon 20 |
| C44-F1 | acaccgcagcataagtcaagat | 11 | Exon 21 |
| C44-R1 | tgcctccttcaatgcatggtat | 12 | Exon 21 |

TABLE 2

Information of probes

| Probe name | Sequence | Seq. no. | Exon | Mutant |
|---|---|---|---|---|
| EP2-2 | FAM-tcaaagtgctgccgcctccggtgc | 13 | Exon 18 | G719A |
| EP3-3 | FAM-aaaagatcaaaccgtgctgagctccg | 14 | Exon 18 | G719S |
| EP4-3 | FAM-aaaagatcaaaccgtgctgtgctccg | 15 | Exon 18 | G719C |
| EP22-1 | FAM-cgtcgctatcaagaagaatcgaaagcca | 16 | Exon 19 | exon 19 deletion |
| EP31-1 | FAM-ccgtcgctatcaaaagtatctccgaaagcca | 17 | Exon 19 | exon 19 deletion |
| EP33-1 | FAM-ccgtcgctatcaaaattccaagaaagccaaca | 18 | Exon 19 | exon 19 deletion |
| EP29-3 | FAM-aagagaagcaacactcgatgtgagtttc | 19 | Exon 19 | exon 19 deletion |
| 2X EP36 | HEX-gcatctgcctcacaactccaccgt | 20 | Exon 20 | QC |
| 2X EP37-Y | FAM-catgagctgcatcgatgagytgca | 21 | Exon 20 | T790M |
| EP48 | HEX-atgcccttcggaacagcctcct | 22 | Exon 20 | C797S |
| EP49 | HEX-atgcccttcggaactccctcct | 23 | Exon 20 | C797S |
| EP50 | HEX-atgcccttcggaagcctcctc | 35 | Exon 20 | C797S |
| EP38-2 | FAM-tacgtgatggccccatcgtggaca | 24 | Exon 20 | S768I |
| EP40-2 | FAM-tggacaaccccaccccacgtgt | 25 | Exon 20 | exon 20 insertion |
| EP41 | FAM-cgtggacccggtaaccccacgtgt | 26 | Exon 20 | exon 20 insertion |
| EP42-2 | FAM-ccagcgcctggacagcgtgg | 27 | Exon 20 | exon 20 insertion |
| EP45 | HEX-cacagattttggccgcgggccaa | 28 | Exon 21 | L858R |
| EP46-3 | HEX-tggccaaccacagctgggtg | 29 | Exon 21 | L861Q |
| EP47-3 | HEX-tttgggcgtgccccaaactg | 30 | Exon 21 | L858R |

When compared with the probes of the prior art (known Patent Application No. 10-2015-0101915), SEQ ID NOs: 13 to 15 and 28 have the same names but differ in the combined fluorescent substance and base sequence, while SEQ ID NOs: 19 to 23 and 35 are probes of new base sequence. Also, SEQ ID NOs: 24 to 27 have the same name and fluorescent substance, but have different base sequences. On the other hand, SEQ ID NOs: 29 and 30 are the same probes as conventional probes.

TABLE 3

Information of blocker oligomers

| Blocker name | Sequence | Seq. no | Exon |
|---|---|---|---|
| E-ex19-B1 | cgtcgctatcaaccggaattaagagaagca | 31 | 19 |
| E-ex21-B1 | gattttgggctgccgccaaact | 32 | 21 |
| E-ex18-B1 | aagtgctgggcctccggtg | 33 | 18 |
| E-C38-B1 | cgtgatggccccagcgtgga | 34 | 20 |

Example 4: Mutation Detection Ability of Primers and Probes

The QX200™ Droplet digital PCR system (Bio-RAD, USA) was used as a ddPCR instrument. For the preparation of the samples, 20 μl were added to 8-strip PCR tubes containing MMX1 mixture, MMX2 mixture, MMX3 mixture and MMX4 mixture, respectively. Further, 1 ul of Ultrapure water (NTC), positive control (PC), and template DNA extracted from patient samples were added to each tube. Information on the MMX1 mixture, MMX2 mixture, MMX3 mixture and MMX4 mixture is shown in Table 4 below. Specific information on primers and probes contained in each MMX is shown in Tables 5 and 6 below.

TABLE 4

Composition of MMX1 mixture, MMX2 mixture, MMX3 mixture and MMX4 mixture

| MMX | EGFR Mutations | Probe | Primer | Flourescent dye |
|---|---|---|---|---|
| 1 | Exon19 del | EP22-1, EP31-1, EP33-1, EP29-3 | C5F15 (forward) C29R1 (reverse) | FAM |

TABLE 4-continued

Composition of MMX1 mixture, MMX2 mixture, MMX3 mixture and MMX4 mixture

| MMX | EGFR Mutations | Probe | Primer | Flourescent dye |
|---|---|---|---|---|
| | QC | 2X EP36 | C36F1 (forward) C36R1 (reverse) | HEX |
| | Blocker | +E-ex19-B1 | | |
| 2 | T790M | 2X EP37-Y | C36F18 (forward) C36R16 (reverse) | FAM |
| | L858R | EP45, EP47-3 | C44F1 (forward) C44R1 (reverse) | HEX |
| | Blocker | +E-ex21-B1 | | |
| 3 | G719X | EP2-2, EP3-3, EP4-3 | C1F1 (forward) C1R1 (reverse) | FAM |

TABLE 4-continued

Composition of MMX1 mixture, MMX2 mixture, MMX3 mixture and MMX4 mixture

| MMX | EGFR Mutations | Probe | Primer | Flourescent dye |
|---|---|---|---|---|
| | C797S | EP48, EP49, EP50 | C36F18 (forward) C36R16 (reverse) | HEX |
| | Blocker | +E-ex18-B1 | | |
| 4 | S768I (DUAL) Exon20 insertions | EP38-2 EP40-2, EP41, EP42-2 | C36F17 (forward) C36R14 (reverse) | FAM |
| | L861Q | 2x EP38-2, EP46-3 | C44F1 (forward) C44R1 (reverse) | HEX |
| | Blocker | +E-C38-B1 | | |

TABLE 5

Information of primers

| | Exon | forward | Start position | Length (bp) | TM | GC% | Amplicon Size (bp) | Reverse | Start position | Length (bp) | TM | GC% |
|---|---|---|---|---|---|---|---|---|---|---|---|---|
| MMX1 | Exon 19 | C5-F15 Sequence gatcccagaaggtgagaaagtta | 119 | 23 | 58.8 | 43.5 | 111 | C29-R1 Sequence aggttcagagccatggac | 229 | 18 | 55.9 | 55.6 |
| | Exon 20 | C36-F1 Sequence ccctccaggaagcctacg | 74 | 18 | 60.75 | 66.67 | 115 | C36-R1 Sequence cagccgaagggcatga | 188 | 16 | 60.47 | 62.50 |
| MMX2 | Exon 20 | C36-F18 Sequence atctgcctcacctccacc | 136 | 18 | 58.5 | 61.1 | 81 | F36-R16 Sequence tttgtgttcccggacatagtc | 216 | 21 | 59.8 | 47.6 |
| | Exon 21 | C44-F1 Sequence acaccgcagcatgtcaagat | 137 | 20 | 61.70 | 50.00 | 85 | C44-R1 Sequence tgcctccttctgcatggtat | 221 | 20 | 60.62 | 50.00 |
| MMX3 | Exon 18 | C1-F1 Sequence tgaggatcttgaaggaaactga | 158 | 22 | 58.91 | 40.91 | 92 | C1-R1 Sequence ctgtgccagggaccttacct | 249 | 20 | 61.46 | 60 |
| | Exon 19 | C36-F18 Sequence atctgcctcacctccacc | 136 | 18 | 58.5 | 61.1 | 81 | F36-R16 Sequence tttgtgttcccggacatagtc | 216 | 21 | 59.8 | 47.6 |
| MMX4 | Exon 20 | C36-F17 Sequence ccacactgacgtgcctct | 72 | 18 | 57.9 | 61.1 | 100 | C36-R14 Sequence ggtggaggtgaggcagat | 171 | 18 | 60.2 | 61.11 |
| | Exon21 | C44-F1 Sequence acaccgcagcatgtcaagat | 137 | 20 | 61.70 | 50.00 | 85 | C44-R1 Sequence tgcctccttctgcatggtat | 221 | 20 | 60.62 | 50.00 |

TABLE 3

Information of probes

| | Name | Sequence | Length (bp) | GC (%) | Tm |
|---|---|---|---|---|---|
| MMX1 | EP22-1 | cgtcgctatcaaggaatcgaaagcca | 26 | 50 | 71.5 |
| | EP31-1 | ccgtcgctatcaagtatctccgaaagcca | 29 | 55 | 73.3 |
| | EP33-1 | ccgtcgctatcaaaattccgaaagccaaca | 30 | 46.7 | 75.4 |
| | EP29-3 | aagagaagcaacactcgatgtgagtttc | 28 | 42.9 | 66.1 |
| | 2X EP36 | gcatctgcctcacctccaccgt | 22 | 63.64 | 70.10 |
| | E-ex19-B1 | cgtcgctatcaaggaattaagagaagca | 28 | 42.9 | 67.3 |
| MMX2 | 2X EP37-Y | catgagctgcatgatgagytgca | 23 | 52.17 | 69.12 |
| | EP45 | cacagattttgggcgggccaa | 21 | 57.14 | 71.20 |
| | EP47-3 | ttttgggcgtgccaaactg | 19 | 52.60 | 65.30 |
| | E-ex21-B1 | gattttgggctggccaaact | 20 | 50 | 63.4 |
| MMX3 | EP2-2 | tcaaagtgctggcctccggtgc | 22 | 63.6 | 72.8 |
| | EP3-3 | aaaagatcaaagtgctgagctccg | 24 | 45.8 | 65.1 |
| | EP4-3 | aaaagatcaaagtgctgtgctccg | 24 | 45.8 | 65.9 |
| | EP48 | atgcccttcggcagcctcct | 20 | 69.6 | 65 |
| | EP49 | atgcccttcggctccctcct | 20 | 68.6 | 65 |
| | EP50 | atgcccttcggaagcctcct | 20 | 69.6 | 65 |
| | E-ex18-B1 | aagtgctgggctccggtg | 18 | 66.7 | 64.8 |

TABLE 3-continued

Information of probes

| | Name | Sequence | Length (bp) | GC (%) | Tm |
|---|---|---|---|---|---|
| MMX4 | EP38-2 | tacgtgatggccatcgtggaca | 22 | 54.5 | 68.9 |
| | EP40-2 | tggacaaccccaccacgtgt | 21 | 61.90 | 70.10 |
| | EP41 | cgtggacggtaaccccacgtgt | 23 | 65.22 | 72.80 |
| | EP42-2 | ccagcgtggacagcgtgg | 18 | 72.2 | 67.6 |
| | EP38-2 | tacgtgatggccatcgtggaca | 22 | 54.5 | 68.9 |
| | EP46-3 | tggccaaacagctgggtg | 18 | 61.10 | 64.30 |
| | E-C38-B1 | cgtgatggccagcgtgga | 18 | 66.7 | 68 |

The 8-Strip PCR tube cap was closed, vortexed, span down, and incubated at room temperature for 10 min. In Droplets Generation step, 20 μl of the prepared samples from 8-Strip PCR tube was loaded into the sample wells of Cartridge using 8-Channel Electronic Pipette. Droplet generation oil was loaded into the oil loading wells of the cartridge by 70 ul, and then the Droplet Generator Gasket was mounted on the top and bottom of the gasket, and the QX200™ Droplet Generator was installed. Droplet generated in the process of droplet generation was transferred to a 96-well plate with 40 μl of droplet using an 8-channel electronic pipette, and Pierceable Foil Heat Seal (BIO-RAD, 181-4040) was covered on to the plate with its red line down, and placed in the PX1™ PCR Plate Sealer (180° C., sealing for 5 sec) and sealed. PCR reaction process was performed using Veriti 96-Well Thermal Cycler. After the PCR reaction, amplified PCR products were separated into FAM and HEX, followed by the process or reading. The resulting product was performed by QuantaSoft software provided by Bio-RAD.

On the other hand, the EGFR mutation sites which can be detected by the MMXs 1 to 4 shown in Table 4 are shown in FIG. 1.

As shown in FIG. 1, the EGFR gene mutation detection kit (Hereinafter referred to as 'GenesWell™ ddEGFR Mutation Test kit') of the present invention comprises all of the MMXs 1 to 4, and each construct shows that it can detect the EGFR mutation site. It can also distinguish mutations with FAM and HEX. For example, 19 deletion mutations in MMX1 of FIG. 1 were used to measure the quality of the sample with FAM, while HEX was used for the EGFR wild type. Therefore, genetic variation was distinguished using FAM and HEX, respectively.

Based on the data published in previous papers, there are shown mutation sites related to the drug reactivity of EGFR tyrosine kinase inhibitor drugs erlotinib, gefitinib, Afatinib and osimertinib. The red color represents the EGFR mutation that is resistant to the drug, while the yellow color represents the EGFR mutation that is reactive on the drug.

Example 5: Mutation Detection Test of GenesWell™ ddEGFR Mutation Test Kit

To determine if the GenesWell™ ddEGFR Mutation Test kit according to the present invention can detect 46 mutation sites of EGFR exons 18-21, 43 standard materials were used. The reason for using 43 reference materials is that the 3 mutation sites contain the same sequence. In addition, considering the heterozygote, which is one of the characteristics of cancer, Miniclone was spiked with 50% of wild type gDNA to prepare a sample. The amount of DNA used in this test was 12 ng/sample, and all 46 samples were reacted with MMX1 to 4 each to perform ddPCR.

As a result, as shown in FIGS. 2A, 2B, 3A, 3B and 3C, only the EGFR mutations detectable by MMX 1 to 4 were detected, and the cross reaction between the mixtures containing the probes was not observed. In addition, cut-off was set based on NTC and gDNA, and mutations were detected when blue or green droplets on the top of the cut-off were detected. In FIGS. 2A, 2B, 3A, 3B and 3C, the types of the mutations represented by blue or green droplets are shown by the clone numbers shown in FIG. 1.

Example 6: Detection Sensitivity of GenesWell™ ddEGFR Mutation Test Kit Using FFPE Samples from Patients To measure the sensitivity of the GenesWell™ ddEGFR Mutation Test kit, DNA derived from FFPE samples of non-small cell lung cancer patients with EGFR mutations was used. For example, samples of patients with 5 exon 19 deletions and 1 L858R mutation were diluted to 0.1, 0.25, 0.5, 1, 1.5 and 3% by spiking with human wild type genomic DNA, while being repeated 24 times at each concentration. Regarding the detection sensitivity, a limit of detection is a concentration in which 95% or more is detected.

Figure 4A:
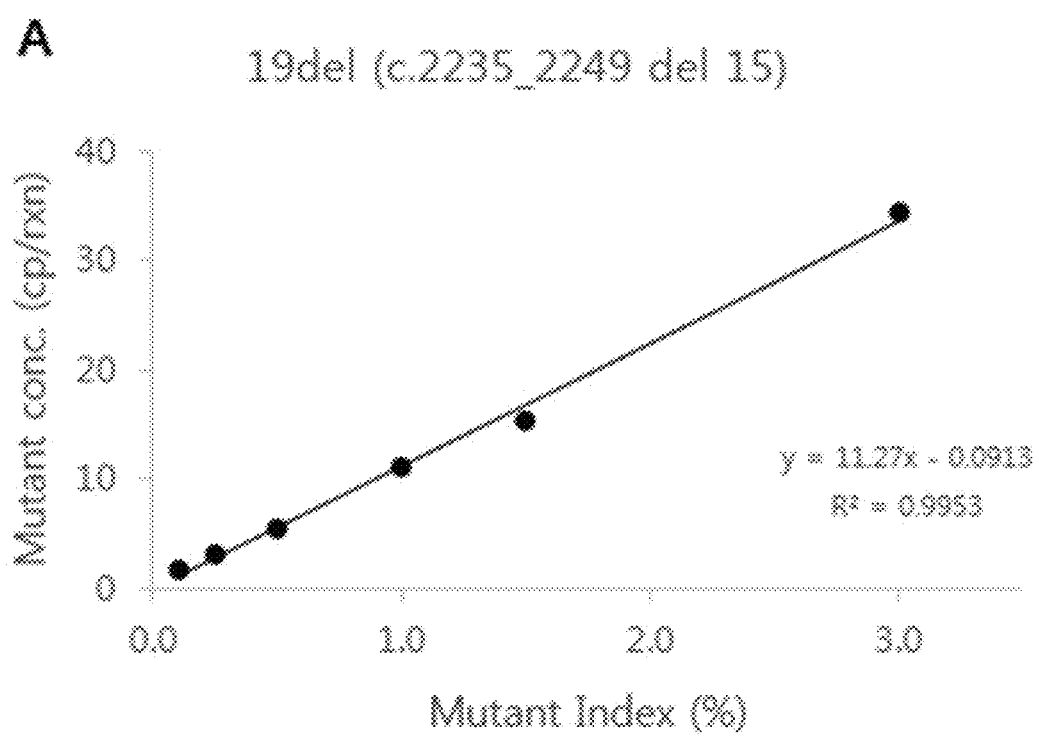
FIGS. 4A and 4B are the results of confirming that the detection sensitivity of the EGFR mutation detection kit comprising a probe and primers according to the present invention using an FFPE sample of a patient having an EGFR mutation (FIG. 4A: 19del(c.2235_2249del15), FIG. 4B: L858R(c.2573_2574T>C)).
Figure 4B:
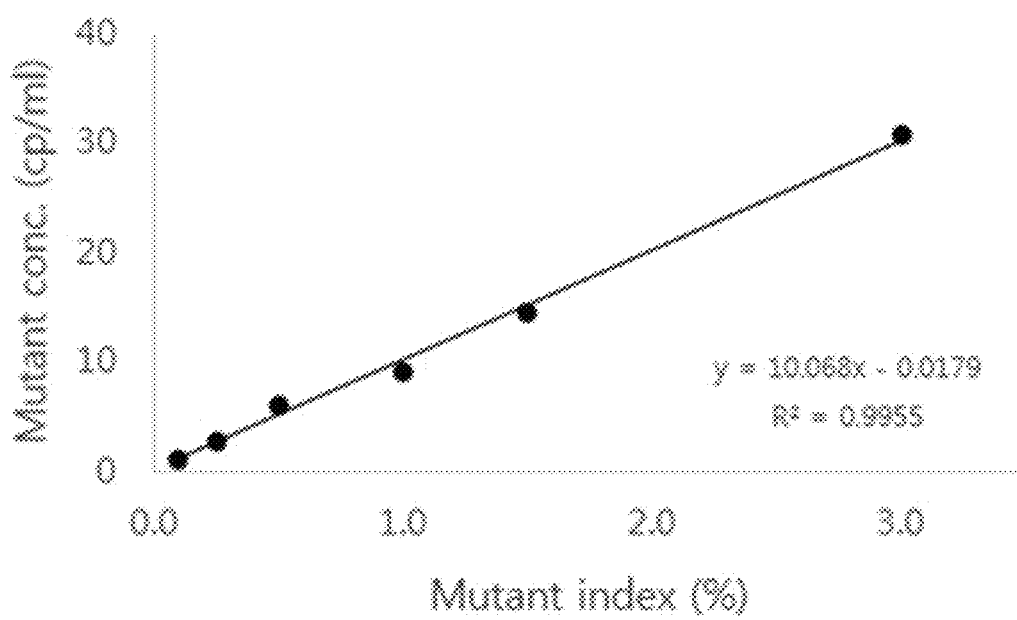

As a result, as shown in Table 7, the detection sensitivity was observed in a range of 0.49% to 1%. More specifically in FIGS. 4A and 4B, for example, the results for detection sensitivity according to EGFR mutation in Exon 19del (c.2235_2249del15) and L858R (c.2573_2574T>G) were schematized. The reliability of each EGFR mutation was 19del (0.9953) and L858R (0.9955).

TABLE 7

GenesWell ™ ddEGFR Mutation Test kit detection sensitivity in patient FFPE samples

| Mutant | Subtype | LOD (%) | Number of Valid Tests | Agreement (N) | Agreement % (95% CI) |
|---|---|---|---|---|---|
| Exon 19 deletion | c.2235_2249 del 15 | 0.74 | 24 | 24 | 100 |
| | c.2238_2252 del 15 | 0.49 | 24 | 24 | 100 |
| | c.2239_2248_TTAAGAGAAG | 0.76 | 24 | 24 | 100 |
| | c.2237_2255T | 1.00 | 24 | 24 | 100 |
| | c.2236_2250 del 15 | 0.81 | 24 | 24 | 100 |

TABLE 7-continued

GenesWell ™ ddEGFR Mutation Test kit detection sensitivity in patient FFPE samples

| Mutant | Subtype | LOD (%) | Number of Valid Tests | Agreement (N) | Agreement % (95% CI) |
|---|---|---|---|---|---|
| Exon21 L858R | c.2573T > G | 0.75 | 24 | 24 | 100 |

Example 7: Mutation Analysis of GenesWell™ ddEGFR Mutation Test Kit for cfDNA and FFPE Samples from the Same Patient EGFR mutations were analyzed and compared using the GenesWell™ ddEGFR Mutation Test kit for FFPE samples and plasma from the same patient.

As a result, as shown in Table 8, the results of the EGFR mutation by the cfDNA isolated from the plasma and the FFPE of 9 patients were found to correspond with each other. Thus, the GenesWell™ ddEGFR Mutation Test kit according to the present, invention may detect EGFR mutation not only in FFPE sample of the patient but also in cfDNA isolated from blood (Liquid biopsy).

according to the present invention is able to monitor both the progress of the disease and the drug responsiveness.

In addition, conventional EGFR kits require about 25 to 50 ng per reaction, whereas the EGFR IUO kit of the present invention is generally able to detect EGFR mutations even in samples of 3 ng as little as 1.5 ng, verifying that this kit according to the present invention is suitable for detecting EGFR mutation in cfDNA.

Example 8: Comparative Analysis of EGFR Mutation Detection Method

IRB-approved clinical samples from hospitals were tested with the GenesWell™ ddEGFR Mutation Test kit and the CobasEGFR mutation test (Roche Molecular Diagnostics, hereinafter referred to as 'cobas kit'), respectively, and the results were compared.

As shown in Table 9, there were samples with mutation which could be detected by the GenesWell™ ddEGFR Mutation Test kit, not by cobas kit.

TABLE 8

Comparison of detected mutations in cfDNA and FFPE samples of the same patient

| | GenesWell ™ ddEGFR Mutation Test | | Local Hospital |
|---|---|---|---|
| Specimen type | Plasma (cfDNA) | | FFPE (Biopsy) |
| Detection Method | ddPCR | | PNA clamp or Sequencing |
| | | Results | |
| Sample ID | Report call | Mut Frequency | Report call |
| BRM-L-P-B-001-1 | L858R/861Q, T790M | 5.16%, 10.94% | Exon21 missensemt |
| BRM-L-P-B-002-1 | T790M, G719X | 2.4%, 4.4% | Exon18 missense mt |
| BRM-L-P-B-003-1* | 19del | 3.74% | Exon19 microdeletion |
| BRM-L-P-B-004-1 | Mut not detected | — | WT |
| BRM-L-P-B-005-1 | 19del | 12.54% | Exon 19 microdeletion |
| BRM-L-P-B-006-1 | L858R/861Q | 64.94% | exon 21 mutation (L858R or L861Q) |
| BRM-L-R-B-020-1 | 19del | 43.01% | exon19 microdeletion, T790M |
| BRM-L-R-B-023-1 | 19del | 81.62% | exon 19 microdeletion; p.E746__A750 |
| BRM-L-R-B-008-1 | Mut not detected | — | exon 19 microdeletion; p.E746__A750, exon 20 missense mutation; p.V769M |
| BRM-L-P-B-003-4* | 19del, T790M | 6.48%, 2.87% | Exon19 microdeletion |

In case of Patient No. 3, blood (Liquid biopsy) was collected at a certain time after the administration of gefitinib for the test. After 5 months of drug administration, the patient did not show any drug responsiveness and blood (Liquid biopsy) was collected for testing. As a result, a drug-resistant T790M mutation was detected. That is, it was verified that the GenesWell™ ddEGFR Mutation Test kit

TABLE 9

Comparison of EGFR mutation detection in GenesWell ™ ddEGFR mutation test and cobas kit

| | | cobas EGFR Test | | | | | | | | | | |
|---|---|---|---|---|---|---|---|---|---|---|---|---|
| (n = 150) | | G719X | 19del | T790M | E20Ins | S768I | L858R | G719X, T790M | G719X, S768I | 19del, T790M | S768I, L858R | MND | Total |
| ddEGFR Test | G719X | 1 | | | | | | | | | | 1 | 2 |
| | 19del | | 61 | | | | | | | | | 1 | 62 |
| | T790M | | | 0 | | | | | | | | | 0 |
| | E20Ins | | | | 0 | | | | | | | 1 | 1 |
| | S768I | | | | | 0 | | | | | | | 0 |

TABLE 9-continued

Comparison of EGFR mutation detection in GenesWell™ ddEGFR mutation test and cobas kit

| (n = 150) | cobas EGFR Test | | | | | | | | | | | |
|---|---|---|---|---|---|---|---|---|---|---|---|---|
| | G719X | 19del | T790M | E20Ins | S768I | L858R | G719X, T790M | G719X, S768I | 19del, T790M | S768I, L858R | MND | Total |
| L858R | | | | | | 41 | | | | | 4 | 45 |
| G719X, T790M | | | | | | | 0 | | | | 1 | 1 |
| G719X, S768I | | | | | | | | 2 | | | | 2 |
| 19del, T790M | | | | | | | | | 0 | | | 3 |
| S768I, L858R | | | | | | | | | | 1 | | 1 |
| MND | | | | | | | | | | | 33 | 33 |
| Total | 1 | 64 | 0 | 0 | 0 | 41 | 0 | 2 | 0 | 1 | 41 | 150 |

Thus, retest was conducted on eight (8) samples with mutation which were detected by the GenesWell™ ddEGFR Mutation Test kit, not by conbas kit. DNA was extracted by macrodissection method in order to increase the proportion of cancer cells in the sample as recommended when the result of the cobas kit was not obtained. The extracted DNA was analyzed with the GenesWell™ ddEGFR Mutation Test kit in the same manner.

As a result, as shown in Table 10, when the mutation that was not previously detected by the cobas kit was macrodissected, it was detected in the same manner as the GenesWell™ ddEGFR Mutation Test kit.

This results confirms that the GenesWell™ ddEGFR Mutation Test kit is able to detect without macrodissection a low percentage of mutations that the cobas kit is unable to detect because of low cancer cell rate, suggesting that the sensitivity and accuracy of the GenesWell™ ddEGFR Mutation Test kit are higher than those of cobas kit.

TABLE 10

Retest results of GenesWell™ ddEGFR Mutation Test kit and cobas kit for mismatched specimens

| Sample NO. | Preliminary result | | | | After Macrodissection | |
|---|---|---|---|---|---|---|
| | cobas | ddEGFR | | Sanger | cobas | ddEGFR |
| 1 | MND | — | MD | L858R | WT | N/A | N/A | N/A | N/A |
| 2 | MND | — | MD | T790M/G719X | Invalid | MND | — | Invalid | — |
| 3 | MND | — | MD | L858R | WT | MD | L858R | MD | L858R |
| 4 | MND | — | MD | G719X | WT | MD | G719X | MD | G719X |
| 5 | MND | — | MD | L858R | WT | MD | L858R | MD | L858R |
| 6 | MND | — | MD | L858R | Wt | N/A | N/A | N/A | N/A |
| 7 | MND | — | MD | 20Ins | WT | MND | — | MD | E20Ins |
| 8 | MND | — | MD | 19del | WT | MD | 19del | MD | 19del |

Example 9: Setting Limits for Quantitative Detection of GenesWell™ ddEGFR Mutation Test Kit in Blood (Liquid Biopsy) Samples For the quantitative limit setting of the GenesWell™ ddEGFR Mutation Test kit, the blank limit and false positive detection values at each mutation were determined using a Human Healthy donor plasma (Hereinafter referred to as HD plasma) without the EGFR mutation. In this experiment, the detection value of EGFR mutation was confirmed using cfDNA extracted from 1 ml of 17 HD plasma, respectively.

Figure 5:
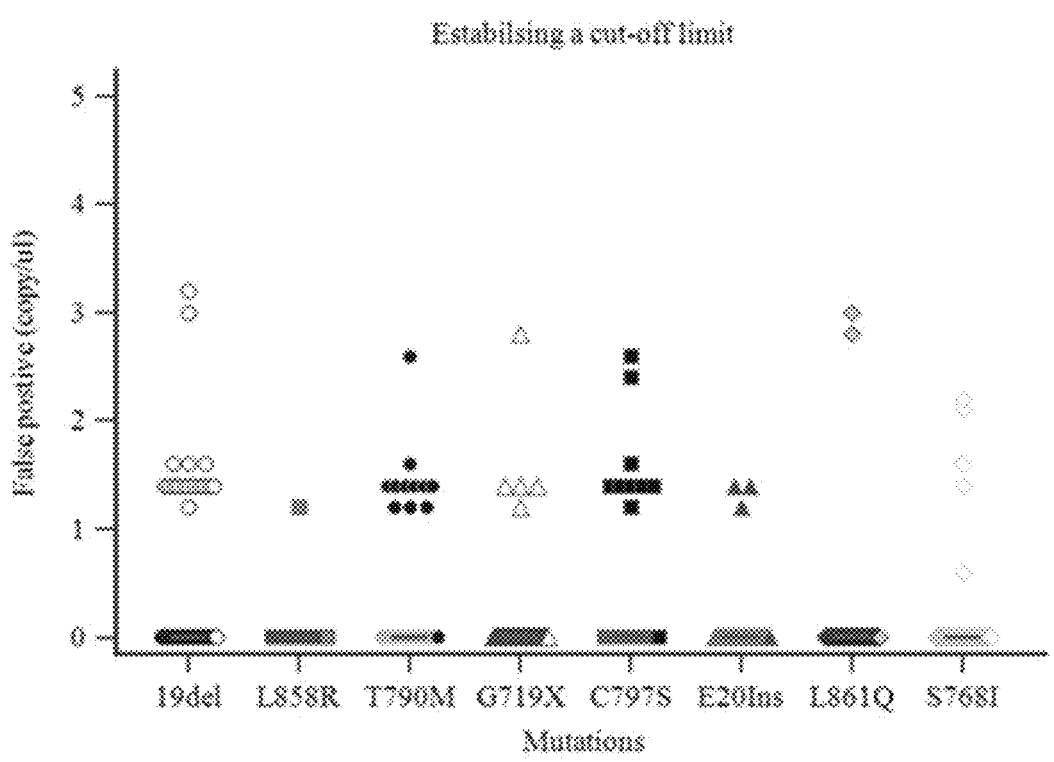
FIG. 5 shows the results of confirming that false positive results of the EGFR mutation detection kit comprising the probe and the primers of the present invention using a blood (Liquid biopsy) sample having no EGFR mutation.

As a result, as shown in FIG. 5, despite the absence of the EGFR mutation in the HD plasma, a maximum of 3.2 copies of the Exon 19 deletion mutation was detected, which was defined as a false positive. Based on these false positive results, the quantitative detection limit of GenesWell™ ddEGFR Mutation Test kit was set to at least 3.3 copies. It was thus determined that there was an existence of an EGFR mutation when the mutation result value derived from the GenesWell™ ddEGFR Mutation Test kit was 3.3 copies or more.

Example 10: Minimal Amount of DNA Necessary for Mutation Detection in Blood Plasma Samples (Liquid Biopsy Samples)

To confirm the minimum range of input DNA of detectable mutation in the plasma sample, DNAs that were artificially produced to resemble cfDNA (hereinafter referred to as contrived DNA) in HD plasma (BIOPREDOC, France) were diluted by concentration and tested. Contrived DNA with EGFR mutation (hereinafter referred to as 'MT contrived DNA') was prepared by fragmenting EGFR reference DNA from Horizon, an internationally recognized reference material, into 200 bp using E220 focused-ultra sonicators (Covaris, USA).

MT contrived DNA was diluted to 100, 75, 50, 25, and 12.5 cp/ml in 1 ml HD plasma, respectively, and cfDNA was extracted using Maxwell CSC equipment (Promega, USA) according to the manufacturer's instructions.

As a result, as shown in Table 11, each EGFR mutation detection sensitivity was confirmed to be at least 0.025% up to maximum 0.05% in 1 ml of HD. More specifically, the GenesWell™ ddEGFR Mutation Test kit is capable of detecting a trace amount of 25 cp (0.08 ng/ml) mutation in 1 ml plasma.

TABLE 11

EGFR mutation detection sensitivity for MT contrived DNA in HD plasma

| Mutant | LOD of Input DNA (cp/ml) | Agreement % (95% CI) | Sensitivity (%) |
|---|---|---|---|
| 19del | 50 | 95.8 | 0.05 |
| T790M | 25 | 95.8 | 0.025 |
| L858R | 50 | 100 | 0.05 |
| G719A | 25 | 100 | 0.025 |
| C797S | 25 | 95.8 | 0.025 |
| 20Ins | 25 | 100 | 0.025 |
| L861Q | 25 | 95.8 | 0.025 |
| S768I | 50 | 100 | 0.05 |

INDUSTRIAL APPLICABILITY

As described above, the method of the present invention makes it possible to predict or diagnose the responsiveness of a cancer patient to a therapeutic agent as well as the prediction of cancer metastasis or recurrence. Therefore, the present invention can be usefully used for judging the necessity of administration of an anti-cancer agent, providing clues about the direction of future treatment and monitoring the metastasis or recurrence of cancer.

What is claimed is:

1. A composition of a set of primers and probes, the composition comprising the following sets as an active ingredient:
   i) a polynucleotide set of a forward primer of SEQ ID NO: 3, a reverse primer of SEQ ID NO: 4, a forward primer of SEQ ID NO: 5, a reverse primer of SEQ ID NO: 6, and probes comprising SEQ ID NOS: 16 to 20;
   ii) a polynucleotide set of a forward primer of SEQ ID NO: 7, a reverse primer of SEQ ID NO: 8, a forward primer of SEQ ID NO: 11, a reverse primer of SEQ ID NO: 12 and probes comprising SEQ ID NOs: 21, 28 and 30;
   iii) a polynucleotide set of a forward primer of SEQ ID NO: 1, a reverse primer of SEQ ID NO: 2, a forward primer of SEQ ID NO: 7, a reverse primer of SEQ ID NO: 8 and probes comprising SEQ ID NOs: 13 to 15, 22, 23 and 35; and
   iv) a polynucleotide set of a forward primer of SEQ ID NO: 9, a reverse primer of SEQ ID NO: 10, a forward primer of SEQ ID NO: 11, a reverse primer of SEQ ID NO: 12, and probes comprising SEQ ID NOS: 24 to 27, 29,
   wherein the probes are bound to a fluorescent material.

2. The composition of claim 1, wherein the fluorescent material is at least one selected from the group consisting of hexachlorofluorescein (HEX), fluorescein amidite (FAM) and EverGreen dye.

3. A kit for detecting an EGFR gene mutation, the kit comprising the composition of claim 1 as an active ingredient.

4. The kit of claim 3, wherein the composition further comprises an oligomer of SEQ ID NO: 31.

5. The kit of claim 3, wherein the composition further comprises an oligomer of SEQ ID NO: 32.

6. The kit of claim 3, wherein the composition further comprises an oligomer of SEQ ID NO: 33.

7. The kit of claim 3, wherein the composition further comprises an oligomer of SEQ ID NO: 34.

8. The kit of claim 3, wherein the kit comprises a cell-free DNA (cfDNA) isolated from blood (Liquid biopsy) as a template.

9. The kit of claim 3, wherein the kit comprises DNA separated from a formalin fixed paraffin embedded (FFPE) tissue, or complementary DNA (cDNA) synthesized by reverse transcription from the tissue-derived RNA as a template.

10. The kit of claim 3, wherein the kit comprises DNA isolated from a circulating tumor cell (CTC) separated from blood (Liquid biopsy) or a complementary DNA (cDNA) synthesized by a reverse transcription from the CTC-derived RNA as a template.

11. A method for detecting an EGFR gene mutation, the method comprising the steps of:
   (a) isolating DNA from a sample;
   (b) performing PCR on the isolated DNA as a template with the composition of claim 1; and
   (c) detecting an epidermal growth factor receptor (EGFR) gene through a product amplified by the PCR.

12. A method for evaluating a therapeutic responsiveness to an EGFR inhibitor in an EGFR inhibitor-administered patient, the method comprising the steps of:
   (a) isolating DNA from a sample obtained from the EGFR inhibitor-administered patient;
   (b) performing PCR on the isolated DNA as a template with the composition of claim 1;
   (c) measuring a mutation index of a product amplified by the PCR;
   (d) comparing the measured mutation index with a previously measured mutation index, thereby determining whether the measured mutation index is decreased or increased; and
   (e) determining the patient has increased resistance to the EGFR inhibitor when there is an increase in the mutation index and determining the patient has maintenance of susceptibility to the EGFR inhibitor when there is a decrease in the mutation index.

13. The method of claim 12, wherein the EGFR inhibitor is selected from the group consisting of erlotinib, gefitinib, Afatinib, osimertinib, and a tyrosine kinase inhibitor targeted for C797S.

* * * * *

SEQUENCE LISTING

<160> NUMBER OF SEQ ID NOS: 35

<210> SEQ ID NO 1
<211> LENGTH: 24
<212> TYPE: DNA
<213> ORGANISM: Artificial Sequence
<220> FEATURE:
<223> OTHER INFORMATION: C1-F1 primer

<400> SEQUENCE: 1
tgaggatctt gaagaagaaa ctga        24

<210> SEQ ID NO 2
<211> LENGTH: 22
<212> TYPE: DNA
<213> ORGANISM: Artificial Sequence
<220> FEATURE:
<223> OTHER INFORMATION: C1-R1 primer

<400> SEQUENCE: 2
ctgtgccaaa gggaccttac ct        22

<210> SEQ ID NO 3
<211> LENGTH: 20
<212> TYPE: DNA
<213> ORGANISM: Artificial Sequence
<220> FEATURE:
<223> OTHER INFORMATION: C5-F15 primer

<400> SEQUENCE: 3
ccctccagga agcctaaacg        20

<210> SEQ ID NO 4
<211> LENGTH: 20
<212> TYPE: DNA
<213> ORGANISM: Artificial Sequence
<220> FEATURE:
<223> OTHER INFORMATION: C29-R1 primer

<400> SEQUENCE: 4
aggttcagag ccatggacaa        20

<210> SEQ ID NO 5
<211> LENGTH: 18
<212> TYPE: DNA
<213> ORGANISM: Artificial Sequence
<220> FEATURE:
<223> OTHER INFORMATION: C36-F1 primer

<400> SEQUENCE: 5

-continued

```
ccctccagga agcctacg                                                    18

<210> SEQ ID NO 6
<211> LENGTH: 16
<212> TYPE: DNA
<213> ORGANISM: Artificial Sequence
<220> FEATURE:
<223> OTHER INFORMATION: C36-R1 primer

<400> SEQUENCE: 6
cagccgaagg gcatga                                                      16

<210> SEQ ID NO 7
<211> LENGTH: 20
<212> TYPE: DNA
<213> ORGANISM: Artificial Sequence
<220> FEATURE:
<223> OTHER INFORMATION: C36-F18 primer

<400> SEQUENCE: 7
ccctccagga agcaactacg                                                  20

<210> SEQ ID NO 8
<211> LENGTH: 23
<212> TYPE: DNA
<213> ORGANISM: Artificial Sequence
<220> FEATURE:
<223> OTHER INFORMATION: F36-R16 primer

<400> SEQUENCE: 8
tttgtgaatt cccggacata gtc                                              23

<210> SEQ ID NO 9
<211> LENGTH: 20
<212> TYPE: DNA
<213> ORGANISM: Artificial Sequence
<220> FEATURE:
<223> OTHER INFORMATION: C36-F17 primer

<400> SEQUENCE: 9
ccacactgac gtgaacctct                                                  20

<210> SEQ ID NO 10
<211> LENGTH: 20
<212> TYPE: DNA
<213> ORGANISM: Artificial Sequence
<220> FEATURE:
<223> OTHER INFORMATION: C36-R14 primer

<400> SEQUENCE: 10
ggtggaggaa tgaggcagat                                                  20

<210> SEQ ID NO 11
<211> LENGTH: 22
<212> TYPE: DNA
<213> ORGANISM: Artificial Sequence
<220> FEATURE:
<223> OTHER INFORMATION: C44-F1 primer

<400> SEQUENCE: 11
acaccgcagc ataagtcaag at                                               22

<210> SEQ ID NO 12
<211> LENGTH: 22
<212> TYPE: DNA
```

```
<213> ORGANISM: Artificial Sequence
<220> FEATURE:
<223> OTHER INFORMATION: C44-R1 primer

<400> SEQUENCE: 12
tgcctccttc aatgcatggt at                                              22

<210> SEQ ID NO 13
<211> LENGTH: 24
<212> TYPE: DNA
<213> ORGANISM: Artificial Sequence
<220> FEATURE:
<223> OTHER INFORMATION: EP2-2 probe

<400> SEQUENCE: 13
tcaaagtgct gccgcctccg gtgc                                            24

<210> SEQ ID NO 14
<211> LENGTH: 26
<212> TYPE: DNA
<213> ORGANISM: Artificial Sequence
<220> FEATURE:
<223> OTHER INFORMATION: EP3-3 probe

<400> SEQUENCE: 14
aaaagatcaa accgtgctga gctccg                                          26

<210> SEQ ID NO 15
<211> LENGTH: 26
<212> TYPE: DNA
<213> ORGANISM: Artificial Sequence
<220> FEATURE:
<223> OTHER INFORMATION: EP4-3 probe

<400> SEQUENCE: 15
aaaagatcaa accgtgctgt gctccg                                          26

<210> SEQ ID NO 16
<211> LENGTH: 28
<212> TYPE: DNA
<213> ORGANISM: Artificial Sequence
<220> FEATURE:
<223> OTHER INFORMATION: EP22-1 probe

<400> SEQUENCE: 16
cgtcgctatc aagaagaatc gaaagcca                                        28

<210> SEQ ID NO 17
<211> LENGTH: 31
<212> TYPE: DNA
<213> ORGANISM: Artificial Sequence
<220> FEATURE:
<223> OTHER INFORMATION: EP31-1 probe

<400> SEQUENCE: 17
ccgtcgctat caaaagtatc tccgaaagcc a                                    31

<210> SEQ ID NO 18
<211> LENGTH: 32
<212> TYPE: DNA
<213> ORGANISM: Artificial Sequence
<220> FEATURE:
<223> OTHER INFORMATION: EP33-1 probe

<400> SEQUENCE: 18
ccgtcgctat caaaattcca agaaagccaa ca                                   32
```

<210> SEQ ID NO 19
<211> LENGTH: 28
<212> TYPE: DNA
<213> ORGANISM: Artificial Sequence
<220> FEATURE:
<223> OTHER INFORMATION: EP29-3 probe

<400> SEQUENCE: 19
aagagaagca acactcgatg tgagtttc                                          28

<210> SEQ ID NO 20
<211> LENGTH: 24
<212> TYPE: DNA
<213> ORGANISM: Artificial Sequence
<220> FEATURE:
<223> OTHER INFORMATION: 2X EP36 probe

<400> SEQUENCE: 20
gcatctgcct cacaactcca ccgt                                              24

<210> SEQ ID NO 21
<211> LENGTH: 24
<212> TYPE: DNA
<213> ORGANISM: Artificial Sequence
<220> FEATURE:
<223> OTHER INFORMATION: 2X EP37-Y probe

<400> SEQUENCE: 21
catgagctgc atcgatgagy tgca                                              24

<210> SEQ ID NO 22
<211> LENGTH: 22
<212> TYPE: DNA
<213> ORGANISM: Artificial Sequence
<220> FEATURE:
<223> OTHER INFORMATION: EP48 probe

<400> SEQUENCE: 22
atgcccttcg gaacagcctc ct                                                22

<210> SEQ ID NO 23
<211> LENGTH: 22
<212> TYPE: DNA
<213> ORGANISM: Artificial Sequence
<220> FEATURE:
<223> OTHER INFORMATION: EP49 probe

<400> SEQUENCE: 23
atgcccttcg gaactccctc ct                                                22

<210> SEQ ID NO 24
<211> LENGTH: 24
<212> TYPE: DNA
<213> ORGANISM: Artificial Sequence
<220> FEATURE:
<223> OTHER INFORMATION: EP38-2 probe

<400> SEQUENCE: 24
tacgtgatgg ccccatcgtg gaca                                              24

<210> SEQ ID NO 25
<211> LENGTH: 23
<212> TYPE: DNA
<213> ORGANISM: Artificial Sequence
<220> FEATURE:

```
<223> OTHER INFORMATION: EP40-2 probe

<400> SEQUENCE: 25
tggacaaccc caccccacg tgt                                         23

<210> SEQ ID NO 26
<211> LENGTH: 25
<212> TYPE: DNA
<213> ORGANISM: Artificial Sequence
<220> FEATURE:
<223> OTHER INFORMATION: EP41 probe

<400> SEQUENCE: 26
cgtggacccg gtaaccccca cgtgt                                      25

<210> SEQ ID NO 27
<211> LENGTH: 20
<212> TYPE: DNA
<213> ORGANISM: Artificial Sequence
<220> FEATURE:
<223> OTHER INFORMATION: EP42-2 probe

<400> SEQUENCE: 27
ccagcgcctg gacagcgtgg                                            20

<210> SEQ ID NO 28
<211> LENGTH: 23
<212> TYPE: DNA
<213> ORGANISM: Artificial Sequence
<220> FEATURE:
<223> OTHER INFORMATION: EP45 probe

<400> SEQUENCE: 28
cacagatttt ggccgcgggc caa                                        23

<210> SEQ ID NO 29
<211> LENGTH: 20
<212> TYPE: DNA
<213> ORGANISM: Artificial Sequence
<220> FEATURE:
<223> OTHER INFORMATION: EP46-3 probe

<400> SEQUENCE: 29
tggccaacca cagctgggtg                                            20

<210> SEQ ID NO 30
<211> LENGTH: 21
<212> TYPE: DNA
<213> ORGANISM: Artificial Sequence
<220> FEATURE:
<223> OTHER INFORMATION: EP47-3 probe

<400> SEQUENCE: 30
ttttgggcgt gccccaaact g                                          21

<210> SEQ ID NO 31
<211> LENGTH: 30
<212> TYPE: DNA
<213> ORGANISM: Artificial Sequence
<220> FEATURE:
<223> OTHER INFORMATION: E-ex19-B1

<400> SEQUENCE: 31
cgtcgctatc aaccggaatt aagagaagca                                 30
```

```
<210> SEQ ID NO 32
<211> LENGTH: 22
<212> TYPE: DNA
<213> ORGANISM: Artificial Sequence
<220> FEATURE:
<223> OTHER INFORMATION: E-ex21-B1

<400> SEQUENCE: 32
gattttgggc tgccgccaaa ct                                                  22

<210> SEQ ID NO 33
<211> LENGTH: 20
<212> TYPE: DNA
<213> ORGANISM: Artificial Sequence
<220> FEATURE:
<223> OTHER INFORMATION: E-ex18-B1

<400> SEQUENCE: 33
aagtgctggg ccctccggtg                                                     20

<210> SEQ ID NO 34
<211> LENGTH: 20
<212> TYPE: DNA
<213> ORGANISM: Artificial Sequence
<220> FEATURE:
<223> OTHER INFORMATION: E-C38-B1

<400> SEQUENCE: 34
cgtgatggcc ccagcgtgga                                                     20

<210> SEQ ID NO 35
<211> LENGTH: 21
<212> TYPE: DNA
<213> ORGANISM: Artificial Sequence
<220> FEATURE:
<223> OTHER INFORMATION: EP50 probe

<400> SEQUENCE: 35
atgcccttcg gaagcctcct c                                                   21
```